(12) United States Patent
George et al.

(10) Patent No.: US 8,150,136 B2
(45) Date of Patent: Apr. 3, 2012

(54) IMAGE BASED QUANTITATION OF MOLECULAR TRANSLOCATION

(75) Inventors: Thaddeus C. George, Seattle, WA (US); David A. Basiji, Seattle, WA (US); Keith Frost, Seattle, WA (US); Brian E. Hall, Seattle, WA (US); William E. Ortyn, Bainbridge Island, WA (US); Michael J. Seo, Mercer Island, WA (US)

(73) Assignee: Amnis Corporation, Seattle, WA (US)

( * ) Notice: Subject to any disclaimer, the term of this patent is extended or adjusted under 35 U.S.C. 154(b) by 833 days.

(21) Appl. No.: 10/593,018

(22) PCT Filed: Mar. 16, 2005

(86) PCT No.: PCT/US2005/008866
§ 371 (c)(1),
(2), (4) Date: Oct. 22, 2008

(87) PCT Pub. No.: WO2005/098430
PCT Pub. Date: Oct. 20, 2005

(65) Prior Publication Data
US 2009/0202130 A1    Aug. 13, 2009

(51) Int. Cl.
*G06K 9/00* (2006.01)
(52) U.S. Cl. ........................................ 382/133
(58) Field of Classification Search .............. None
See application file for complete search history.

(56) References Cited

U.S. PATENT DOCUMENTS

| | | | |
|---|---|---|---|
| 3,497,690 A | 2/1970 | Gunter et al. | 250/461.2 |
| 3,555,280 A | 1/1971 | Richards, Jr. | 250/201 |
| 3,586,760 A | 6/1971 | Dillenburger | 348/339 |
| 3,922,069 A | 11/1975 | Kishikawa et al. | 350/173 |
| 4,313,734 A | 2/1982 | Leuvering | 23/230 |
| 4,414,575 A | 11/1983 | Yamamoto et al. | 348/350 |
| 4,635,293 A | 1/1987 | Watanabe | 382/44 |
| 4,662,742 A | 5/1987 | Chupp | 356/39 |
| 4,677,680 A | 6/1987 | Harima et al. | 382/1 |
| 4,703,017 A | 10/1987 | Campbell et al. | 436/501 |
| 4,737,932 A | 4/1988 | Baba | 364/900 |
| 4,770,992 A | 9/1988 | Van den Engh et al. | 435/6 |
| 4,777,525 A | 10/1988 | Preston, Jr. | 358/102 |
| 4,786,165 A | 11/1988 | Yamamoto et al. | 356/23 |
| 4,845,197 A | 7/1989 | Petersen et al. | 530/387 |
| 4,857,453 A | 8/1989 | Ullman et al. | 435/7 |
| 4,959,302 A | 9/1990 | Cornaby et al. | 435/5 |
| 5,096,807 A | 3/1992 | Leaback | 435/6 |
| 5,107,522 A | 4/1992 | Kitayama et al. | 375/97 |

(Continued)

FOREIGN PATENT DOCUMENTS
EP    0 154 404    9/1985
(Continued)

OTHER PUBLICATIONS

Oberholzer et al., "Methods in quantitative image analysis." *Histochem Cell Biol*, vol. 105: 333-355, 1996.

(Continued)

*Primary Examiner* — Roberto Velez
(74) *Attorney, Agent, or Firm* — Law Office of Ronald M. Anderson

(57) ABSTRACT

The use of an imaging system, cell compartment markers, and molecular markers in methods for correlating the movement of molecules within a cell to a particular compartment are provided, including measuring and correlating molecule movement in adherent and non-adherent cells.

18 Claims, 15 Drawing Sheets

U.S. PATENT DOCUMENTS

| | | | | |
|---|---|---|---|---|
| 5,122,453 | A | 6/1992 | Martin et al. | 435/7.24 |
| 5,141,609 | A | 8/1992 | Sweedler et al. | 204/180.1 |
| 5,153,916 | A | 10/1992 | Inagaki et al. | 382/4 |
| 5,159,397 | A | 10/1992 | Kosaka et al. | 356/73 |
| 5,159,398 | A | 10/1992 | Maekawa et al. | 356/73 |
| 5,159,642 | A | 10/1992 | Kosaka | 382/134 |
| 5,247,339 | A | 9/1993 | Ogino | 356/73 |
| 5,247,340 | A | 9/1993 | Ogino | 356/73 |
| 5,257,182 | A | 10/1993 | Luck et al. | 364/413.1 |
| 5,272,354 | A | 12/1993 | Kosaka | 250/574 |
| 5,351,311 | A | 9/1994 | Rogers et al. | 382/45 |
| 5,372,936 | A | 12/1994 | Fraatz et al. | 435/34 |
| 5,422,712 | A | 6/1995 | Ogino | 356/73 |
| 5,436,144 | A | 7/1995 | Stewart et al. | 435/91.2 |
| 5,444,527 | A | 8/1995 | Kosaka | 356/73 |
| 5,459,240 | A | 10/1995 | Foxwell et al. | 530/328 |
| 5,471,294 | A | 11/1995 | Ogino | 356/73 |
| 5,547,849 | A | 8/1996 | Baer et al. | 435/7.24 |
| 5,548,349 | A | 8/1996 | Mizuguchi et al. | 348/766 |
| 5,548,395 | A | 8/1996 | Kosaka | 356/73 |
| 5,568,315 | A | 10/1996 | Shuman | 359/487 |
| 5,596,401 | A | 1/1997 | Kusuzawa | 356/23 |
| 5,621,460 | A | 4/1997 | Hatlestad et al. | 348/265 |
| 5,625,048 | A | 4/1997 | Tsien et al. | 536/23.4 |
| 5,633,503 | A | 5/1997 | Kosaka | 250/458.1 |
| 5,644,388 | A | 7/1997 | Maekawa et al. | 356/73 |
| 5,674,743 | A | 10/1997 | Ulmer | 435/287.2 |
| 5,686,960 | A | 11/1997 | Sussman et al. | 348/335 |
| 5,695,934 | A | 12/1997 | Brenner | 435/6 |
| 5,733,721 | A | 3/1998 | Hemstreet, III et al. | 435/6 |
| 5,754,291 | A | 5/1998 | Kain | 356/338 |
| 5,760,899 | A | 6/1998 | Eismann | 356/326 |
| 5,764,792 | A | 6/1998 | Kennealy | 382/133 |
| 5,784,162 | A | 7/1998 | Cabib et al. | 356/456 |
| RE35,868 | E | 8/1998 | Kosaka | 250/574 |
| 5,828,776 | A | 10/1998 | Lee et al. | 382/133 |
| 5,831,723 | A | 11/1998 | Kubota et al. | 356/73 |
| 5,844,670 | A | 12/1998 | Morita et al. | 356/124 |
| 5,848,123 | A | 12/1998 | Strommer | 378/98.8 |
| 5,855,753 | A | 1/1999 | Trau et al. | 204/484 |
| 5,900,942 | A | 5/1999 | Spiering | 356/400 |
| 5,926,283 | A | 7/1999 | Hopkins | 356/419 |
| 5,929,986 | A | 7/1999 | Slater et al. | 356/326 |
| 5,939,281 | A | 8/1999 | Lehmann et al. | 435/7.94 |
| 5,959,953 | A | 9/1999 | Alon | 369/44.41 |
| 5,965,366 | A | 10/1999 | Ochoa et al. | 435/6 |
| 5,985,549 | A | 11/1999 | Singer et al. | 435/6 |
| 5,986,061 | A | 11/1999 | Pestka | 530/352 |
| 6,007,994 | A | 12/1999 | Ward et al. | 435/6 |
| 6,007,996 | A | 12/1999 | McNamara et al. | 435/6 |
| 6,014,468 | A | 1/2000 | McCarthy et al. | 382/254 |
| 6,066,459 | A | 5/2000 | Garini et al. | 435/6 |
| 6,108,082 | A | 8/2000 | Pettipiece et al. | 356/301 |
| 6,115,119 | A | 9/2000 | Sieracki et al. | 356/337 |
| 6,116,739 | A | 9/2000 | Ishihara et al. | 353/31 |
| 6,150,121 | A | 11/2000 | Hamawy et al. | 435/7.24 |
| 6,156,465 | A | 12/2000 | Cao et al. | 430/30 |
| 6,159,686 | A | 12/2000 | Kardos et al. | 435/6 |
| 6,210,973 | B1 | 4/2001 | Pettit | 436/172 |
| 6,211,955 | B1 | 4/2001 | Basiji et al. | 356/326 |
| 6,229,913 | B1 | 5/2001 | Nayar et al. | 382/154 |
| 6,249,314 | B1 | 6/2001 | Yamamoto et al. | 348/242 |
| 6,249,341 | B1 | 6/2001 | Basiji et al. | 356/73 |
| 6,256,096 | B1 | 7/2001 | Johnson | 356/335 |
| 6,259,807 | B1 | 7/2001 | Ravkin | 381/133 |
| 6,330,081 | B1 | 12/2001 | Scholten | 358/463 |
| 6,330,361 | B1 | 12/2001 | Mitchell et al. | 382/211 |
| 6,381,363 | B1 | 4/2002 | Murching et al. | 382/164 |
| 6,473,176 | B2 | 10/2002 | Basiji et al. | 356/326 |
| 6,507,391 | B2 | 1/2003 | Riley et al. | 356/28 |
| 6,510,319 | B2 | 1/2003 | Baum et al. | 455/442 |
| 6,519,355 | B2 | 2/2003 | Nelson | 382/133 |
| 6,522,781 | B1 | 2/2003 | Norikane et al. | 382/203 |
| 6,532,061 | B2 | 3/2003 | Ortyn et al. | 356/28 |
| 6,548,259 | B2 | 4/2003 | Ward et al. | 435/6 |
| 6,549,664 | B1 | 4/2003 | Daiber et al. | 382/232 |
| 6,563,583 | B2 | 5/2003 | Ortyn et al. | 356/400 |
| 6,580,504 | B1 | 6/2003 | Basiji et al. | 356/338 |
| 6,583,865 | B2 | 6/2003 | Basiji et al. | 356/73 |
| 6,608,680 | B2 | 8/2003 | Basiji et al. | 356/338 |
| 6,608,682 | B2 | 8/2003 | Ortyn et al. | 356/419 |
| 6,618,140 | B2 | 9/2003 | Frost et al. | 356/317 |
| 6,620,591 | B1 | 9/2003 | Dunlay et al. | 435/7.2 |
| 6,658,143 | B2 | 12/2003 | Hansen et al. | 382/133 |
| 6,671,044 | B2 | 12/2003 | Ortyn et al. | 356/326 |
| 6,671,624 | B1 | 12/2003 | Dunlay et al. | 702/19 |
| 6,707,551 | B2 | 3/2004 | Ortyn et al. | 356/338 |
| 6,716,588 | B2 | 4/2004 | Sammak et al. | 435/7.23 |
| 6,727,066 | B2 | 4/2004 | Kaser | 435/6 |
| 6,763,149 | B2 | 7/2004 | Riley et al. | 382/294 |
| 6,778,263 | B2 | 8/2004 | Ortyn et al. | 356/28 |
| 6,873,733 | B2 | 3/2005 | Dowski, Jr. | 382/232 |
| 6,875,973 | B2 | 4/2005 | Ortyn et al. | 250/201.3 |
| 6,906,792 | B2 | 6/2005 | Ortyn et al. | 356/28.5 |
| 6,927,922 | B2 | 8/2005 | George et al. | 359/708 |
| 6,934,408 | B2 | 8/2005 | Frost et al. | 382/129 |
| 6,947,128 | B2 | 9/2005 | Basiji et al. | 356/73 |
| 6,947,136 | B2 | 9/2005 | Ortyn et al. | 356/338 |
| 6,975,400 | B2 | 12/2005 | Ortyn et al. | 356/419 |
| 7,006,710 | B2 | 2/2006 | Riley et al. | 382/294 |
| 7,033,819 | B2 | 4/2006 | Kim et al. | 435/29 |
| 7,042,639 | B1 | 5/2006 | McDowell | 359/398 |
| 7,050,620 | B2 | 5/2006 | Heckman | 382/133 |
| 7,057,732 | B2 | 6/2006 | Jorgenson et al. | 356/445 |
| 7,079,708 | B2 | 7/2006 | Riley et al. | 382/294 |
| 7,087,877 | B2 | 8/2006 | Ortyn et al. | 250/201.2 |
| 7,139,415 | B2 | 11/2006 | Finkbeiner | 382/128 |
| 7,180,673 | B2 | 2/2007 | Dowski, Jr. | 359/637 |
| 7,190,832 | B2 | 3/2007 | Frost et al. | 382/173 |
| 7,221,457 | B2 | 5/2007 | Jorgenson et al. | 356/445 |
| 7,289,205 | B2 | 10/2007 | Yaroslavsky et al. | 356/417 |
| 7,306,921 | B2 | 12/2007 | Nevalainen et al. | 435/7.1 |
| 7,315,357 | B2 | 1/2008 | Ortyn et al. | 356/73 |
| 7,450,229 | B2 | 11/2008 | Ortyn et al. | 356/326 |
| 7,476,514 | B2 | 1/2009 | Britz et al. | 435/7.24 |
| 7,567,695 | B2 | 7/2009 | Frost et al. | 382/129 |
| 7,667,761 | B2 | 2/2010 | Thomas | 348/335 |
| 2001/0006416 | A1 | 7/2001 | Johnson | 356/73 |
| 2001/0012620 | A1 | 8/2001 | Rich | 435/7.1 |
| 2002/0126275 | A1 | 9/2002 | Johnson | 356/317 |
| 2002/0146734 | A1 | 10/2002 | Ortyn et al. | 435/6 |
| 2003/0048931 | A1 | 3/2003 | Johnson et al. | 382/128 |
| 2003/0049701 | A1 | 3/2003 | Muraca | 435/7.23 |
| 2003/0059093 | A1 | 3/2003 | Rosania et al. | 382/128 |
| 2003/0104439 | A1 | 6/2003 | Finch | 435/6 |
| 2004/0093166 | A1 | 5/2004 | Kil | 702/19 |
| 2004/0111220 | A1 | 6/2004 | Ochs et al. | 702/19 |
| 2004/0241759 | A1 | 12/2004 | Tozer et al. | 435/7.2 |
| 2005/0014129 | A1 | 1/2005 | Cliffel et al. | 435/4 |
| 2006/0246481 | A1 | 11/2006 | Finch et al. | 435/6 |
| 2006/0257884 | A1 | 11/2006 | Brawley et al. | 435/6 |
| 2007/0054350 | A1 | 3/2007 | Walker, Jr. | 435/34 |
| 2007/0122806 | A1 | 5/2007 | Strom et al. | 435/6 |
| 2008/0240539 | A1 | 10/2008 | George et al. | 382/133 |
| 2009/0088409 | A1 | 4/2009 | Charlton | 514/171 |

FOREIGN PATENT DOCUMENTS

| | | |
|---|---|---|
| EP | 0 280 559 | 8/1988 |
| EP | 0 281 327 | 6/1993 |
| EP | 0 372 707 | 3/1996 |
| EP | 0 950 890 | 10/1999 |
| EP | 1 316 793 | 6/2003 |
| WO | WO 88/08534 | 11/1988 |
| WO | WO 90/10715 | 9/1990 |
| WO | WO 95/20148 | 7/1995 |
| WO | WO 97/26333 | 7/1997 |
| WO | WO 98/53093 | 11/1998 |
| WO | WO 98/53300 | 11/1998 |
| WO | WO 99/24458 | 5/1999 |
| WO | WO 99/64592 | 12/1999 |
| WO | WO 00/06989 | 2/2000 |
| WO | WO 00/14545 | 3/2000 |
| WO | WO 00/42412 | 7/2000 |
| WO | WO 01/11341 | 2/2001 |
| WO | WO 01/46675 | 6/2001 |
| WO | WO 02/17622 | 2/2002 |
| WO | WO 02/18537 | 3/2002 |

| WO | WO 02/31182 | 4/2002 |
| WO | WO 02/35474 | 5/2002 |
| WO | WO 02/073200 | 9/2002 |
| WO | WO 02/079391 | 10/2002 |
| WO | WO 2005/090945 | 9/2005 |
| WO | WO 2005/098430 | 10/2005 |

OTHER PUBLICATIONS

Ferraro et al., "Extended focused image in microscopy by digital holography."*Optics Express*, vol. 13, No. 18: 6738-6749, 2005.

Colombo et al., "Biopsy coupled to quantitative immunofluorescence: a new method to study the human vascular endothelium." *Journal of Applied Physiology*, vol. 92: 1331-1338, 2002.

Giese et al., "Monitoring of NFAT-regulated gene expression in the peripheral blood of allograft recipients: a novel perspective towards individually optimized drug doses of cyclosporine A." *Transplantation*, vol. 77, No. 3: 339-344, 2004.

Hartel et al., "Delayed cytokine mRNA expression kinetics after T-lymphocyte costimulation: a quantitative measure of the efficacy of cyclosporine A-based immunosuppression." *Clinical Chemistry*: 10 pp., 2002.

Manna et al., "Immunosuppressive Leflunomide Metabolite (A77 1726) Blocks TNF-Dependent Nuclear Factor—κB Activation and Gene Expression." *The Journal of Immunology*, vol. 162: 2095-2102, 1999.

Wong et al., "Prognostic and Diagnostic Significance of Beta-Catenin Nuclear Immunostaining in Colorectal Cancer." *Clinical Cancer Research*, vol. 10: 1401-1408, 2004.

Amann et al., "Fluorescent-Oligonucleotide Probing of Whole Cells for Determinative, Phylogenetic, and Environmental Studies in Microbiology," *Journal of Bacteriology* vol. 172, No. 2: 762-770, Feb. 1990.

Arkesteijn et al., "Chromosome Specific DNA Hybridization in Suspension for Flow Cytometric Detection of Chimerism in Bone Marrow Transplantation and Leukemia," *Cytometry* 19: 353-360, Apr. 1995.

Bains et al., "Flow Cytometric Quantitation of Sequence-Specific mRNA in Hemopoietic Cell Suspension by Primer-Induced in Situ (PRINS) Fluorescent Nucleotide Labeling," *Experimental Cell Research* 208: 321-326, Sep. 1993.

Barren III et al., "Method for Identifying Prostate Cells in Semen Using Flow Cytometry," *The Prostate* 36: 181-188, 1998.

Bauman et al., "Flow Cytometric Detection of Ribosomal RNA in Suspended Cells by Fluorescent In Situ Hybridization," *Cytometry* 9: 517-524, 1988.

Baumgartner et al., "Automated Evaluation of Frequencies of Aneuploid Sperm by Laser-Scanning Cytometry (LSC)," *Cytometry* 44: 156-160, 2001.

Ben-Eliezer et al., "All-optical extended depth of field imaging system," *Journal of Optics A: Pure and Applied Optics* 5: S164-S169, 2003.

Biggs et al., "Acceleration of iterative image restoration algorithms" *Applied Optics* vol. 36, No. 8: 1766-1775, Mar. 10, 1997.

Boyle et al., "Isolation and Initial Characterization of a Large Repeat Sequence Element Specific to Mouse Chromosome 8," *Genomics* vol. 12, No. 3: 517-525, 1992.

Callet-Bauchu et al., "Distribution of the cytogenetic abnormality +i(3)(q10) in persistent polyclonal B-cell lymphocytosis: a FICTION study in three cases," *British Journal of Haematology* 99: 531-536, Dec. 1997.

Ding et al., "Characterization and Quantitation of NF-κB Nuclear Translocation Induced by Interleukin-1 and Tumor Necrosis Factor-α," *The Journal of Biological Chemistry* vol. 273, No. 44: 28897-28905, Oct. 30, 1998.

Disteche et al., "Isolation and characterization of two repetitive DNA fragments located near the centromere of the mouse X chromosome," *Cytogenetics and Cell Genetics* 39: 262-268, 1985.

Dragowska et al., "Measurement of DNA repeat sequence by flow cytometry," *Cytometry* Supplement 7: 51, Oct. 1994.

Engvall, Eva. "Enzyme Immunoassay ELISA and EMIT," *Methods in Enzymology* vol. 70, Part A: 419-439, 1980.

Fernandez-Lago et al., "Fluorescent Whole-Cell Hybridization with 16S rRNA-Targeted Oligonucleotide Probes To Identify *Brucella* spp. by Flow Cytometry." *Journal of Clinical Microbiology* vol. 38, No. 7: 2768-2771, Jul. 2000.

George et al., "Extended depth of field using a logarithmic asphere" *Journal of Optics A: Pure and Applied Optics* 5: S157-S163, 2003.

George et al., "Distinguishing Modes of Cell Death Using the ImageStream® Multispectral Imaging Flow Cytometer," *Cytometry Part A* 59A: 237-245, 2004.

George et al., "Quantitative measurement of nuclear translocation events using similarity analysis of multispectral cellular images obtained in flow," *Journal of Immunological Methods* 311: 117-129, 2006.

Gordy et al., "Visualization of Antigen Presentation by Actin-Mediated Targeting of Glycolipid-Enriched Membrane Domains to the Immune Synapse of B cell APCs." *Journal of Immunology* vol. 172, No. 4: 2030-2038, Feb. 15, 2004.

Hecht, Eugene. "Optics 4$^{th}$ ed." Addison-Wesley Longman, Inc., XP-002465391, ISBN: 0-8053-8566-5, 2002.

Hultdin et al., "Telomere analysis by fluorescence in situ hybridization and flow cytometry," *Nucleic Acids Research* vol. 26, No. 16: 3651-3656, Aug. 15, 1998.

Kubota et al., "Flow Cytometer and Imaging Device Used in Combination." *Cytometry* 21: 129-132, 1995.

Kubota, Fumio. "Analysis of red cell and platelet morphology using an imaging-combined flow cytometer." *Clin. Lab. Haem.* 25: 71-76, 2003.

Lauzon et al., "Flow Cytometric Measurement of Telomere Length," *Cytometry* 42: 159-164, Jun. 2000.

Levron et al., "Sperm chromosome abnormalities in men with severe male factor infertility who are undergoing in vitro fertilization with intracytoplasmic sperm injection," *Fertility and Sterility* vol. 76, No. 3: 479-484, Sep. 2001.

Lowe et al., "Aneuploid epididymal sperm detected in chromosomally normal and Robertsonian translocation-bearing mice using a new three-chromosome FISH method," *Chromosoma* 105: 204-210, 1996.

Majno et al., "Apoptosis, Oncosis, and Necrosis *An Overview of Cell Death*," *American Journal of Pathology* vol. 146, No. 1: 3-15, Jan. 1, 1995.

Martin et al., "Detection of aneuploidy in human interphase spermatozoa by fluorescence in situ hybridization (FISH)," *Cytogenetics and Cell Genetics* 64: 23-26, 1993.

Nautiyal et al., "17β-Estradiol induces nuclear translocation of CrkL at the window of embryo implantation," *Biochemical and Biophysical Research Communications* 318: 103-112, 2004.

Ong, Sim Heng, "Development of a System for Imaging and Classifying Biological Cells in a Flow Cytometer," Doctor of Philosophy Thesis, University of Sydney, School of Electrical Engineering, Aug. 1985.

Ong et al., "Development of an Image Flow Cytometer," *Analytical and Quantitative Cytology and Histology*. XIVth International Conference on Medical and Biological Engineering and the VIIth International Conference on Medical Physics, Finland: 375-382, Aug. 1987.

Ong et al., "Optical Design in a Flow System for Imaging Cells," *Sciences in Medicine*, vol. 14, No. 2: 74-80, 1991.

Ong et al., "Analysis of MTF Degradation in the Imaging of Cells in a Flow System," *International Journal of Imaging Systems & Technology* 5: 243-250, 1994.

Ortyn et al., "Extended Depth of Field Imaging for High Speed Cell Analysis" *Cytometry Part A* 71A: 215-231, 2007.

Pala et al., "Flow cytometric measurement of intracellular cytokines," *Journal of Immunological Methods* 243: 107-124, 2000.

Pang et al., "Detection of aneuploidy for chromosomes 4, 6, 7, 8, 9, 10, 11, 12, 13, 17, 18, 21, X and Y by fluorescence in-situ hybridization in spermatozoa from nine patients with oligoasthenoteratozoospermia undergoing intracytoplasmic sperm injection," *Human Reproduction* vol. 14, No. 5: 1266-1273, 1999.

Patterson et al., "Detection of HIV-1 DNA and Messenger RNA in Individual Cells by PCR-Driven in Situ Hybridization and Flow Cytometry," *Science* 260: 976-979, May 14, 1993.

Perreault et al., "The Role of Disulfide Bond Reduction during Mammalian Sperm Nuclear Decondensation in Vivo," *Developmental Biology* 101: 160-167, 1984.

Pinkel et al., "Cytogenetic analysis using quantitative, high sensitivity, fluorescence hybridization," *Proceedings of the National Academy of Sciences: Genetics* 83: 2934-2938, 1986.

Pollice et al., "Sequential Paraformaldehyde and Methanol Fixation for Simultaneous Flow Cytometric Analysis of DNA, Cell Surface Proteins, and Intracellular Proteins," *Cytometry* 13: 432-444, 1992.

Ried et al., "Simultaneous visualization of seven different DNA probes by in situ hybridization using combinatorial fluorescence and digital imaging microscopy," *Proceedings of the National Academy of Sciences: Genetics* 89: 1388-1392, Feb. 1992.

Robbins et al., "Aneuploidy in sperm of Hodgkin's disease patients receiving NOVP chemotherapy," *The American Journal of Human Genetics* vol. 55, No. 3—Supplement: A68 (371), Sep. 1994.

Robbins et al., "Detection of Aneuploid Human Sperm by Fluorescence In Situ Hybridization: Evidence for a Donor Difference in Frequency of Sperm Disomic for Chromosomes I and Y," *The American Journal of Human Genetics*, 52: 799-807, 1993.

Robbins et al., "Three-probe Fluorescence in situ Hybridization to Assess Chromosome X, Y, and 8 Aneuploidy in Sperm of 14 Men from Two Healthy Groups: Evidence for a Paternal Age Effect on Sperm Aneuploidy," *Reproduction, Fertility and Development* 7: 799-809, 1995.

Robbins et al., "Use of Fluorescence In Situ Hybridization (FISH) To Assess Effects of Smoking, Caffeine, and Alcohol on Aneuploidy Load in Sperm of Healthy Men," *Environmental and Molecular Mutagenesis* 30: 175-183, 1997.

Rufer et al., "Telomere length dynamics in human lymphocyte subpopulations measured by flow cytometry," *Nature Biotechnology* 16: 743-747, Aug. 1998.

Salzman et al., "Light Scatter: Detection and Usage," *Current Protocols in Cytometry* Supplement 9: 1.13.1-1.138.8, 1999.

Satoh et al., "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry* 48: 194-201, 2002.

Schmid et al., "Evaluation of inter-scorer and inter-laboratory reliability of the mouse epididymal sperm aneuploidy (m-ESA) assay," *Mutagenesis* vol. 16, No. 3: 189-195, 2001.

Schmid et al., "Simultaneous Flow Cytometric Analysis of Two Cell Surface Markers, Telomere Length, and DNA Content," *Cytometry* 49: 96-105, 2002.

Schwerin et al., "Quantification of Y Chromosome Bearing Spermatozoa of Cattle Using In Situ Hybridization," *Molecular Reproduction and Development* 30: 39-43, 1991.

Shi et al., "Aneuploidy in human sperm: a review of the frequency and distribution of aneuploidy, effects of donor age and lifestyle factors," *Cytogenetics and Cell Genetics* 90: 219-226, 2000.

Timm et al., "Amplification and Detection of a Y-Chromosome DNA Sequence by Fluorescence In Situ Polymerase Chain Reaction and Flow Cytometry Using Cells in Suspension," *Cytometry (Communications in Clinical Cytometry)* 22: 250-255, 1995.

Timm et al., "Fluorescent In Situ Hybridization En Suspension (FISHES) Using Digoxigenin-qLabeled Probes and Flow Cytometry," *Biotechniques* vol. 12, No. 3: 362-367, 1992.

Trask et al., "Fluorescence in situ hybridization to interphase cell nuclei in suspension allows flow cytometric analysis of chromosome content and microscopic analysis of nuclear organization," *Human Genetics* 78:251-259, 1988.

Tucker et al., "Extended depth of field and aberration control for inexpensive digital microscope systems" *Optics Express* vol. 4, No. 11: 467-474, May 24, 1999.

van Dekken et al., "Flow Cytometric Quantification of Human Chromosome Specific Repetitive DNA Sequences by Single and Bicolor Fluorescent In Situ Hybridization to Lymphocyte Interphase Nuclei," *Cytometry* 11: 153-164, 1990.

van den Berg et al., "Detection of Y Chromosome by in situ Hybridization in Combination with Membrane Antigens by Two-Color Immunofluorescence," *Laboratory Investigation* vol. 64, No. 5: 623-628, 1991.

Wang et al., "A Novel Apoptosis Research Method With Imaging-Combined Flow Cytometer and HITC OR IR-125 Staining," *Cytometry (Clinical Cytometry)* 50: 267-274, 2002.

Weber-Matthieson et al., "Rapid immunophenotypic characterization of chromosomally aberrant cells by the new FICTION method," *Cytogenetics Cell Genetics* 63: 123-125, 1993.

Weber-Matthieson et al., "Simultaneous Fluorescence Immunophenotyping and Interphase Cytogenetics: A Contribution to the Characterization of Tumor Cells," *Journal of Histochemistry and Cytochemistry* vol. 40, No. 2: 171-175, 1992.

Wietzorrek et al., "A New Multiparameter Flow Cytometer: Optical and Electrical Cell Analysis in Combination With Video Microscopy in Flow," *Cytometry* 35: 291-301, 1999.

Wyrobek et al., "Smokers produce more aneuploid sperm than non-smokers," *The American Society of Human Genetics*, 45th Annual Meeting, A131: 737, Oct. 24-28, 1995.

Wyrobek et al., "Detection of Sex Chromosomal Aneuploidies X-X, Y-Y, and X-Y, in Human Sperm Using Two-Chromosome Fluorescence In Situ Hybridization," *American Journal of Medical Genetics* 53: 1-7, 1994.

Wyrobek et al., "Fluorescence In Situ Hybridization to Y Chromosomes in Decondensed Human Sperm Nuclei," *Molecular Reproduction and Development* 27: 200-208, 1990.

Ferraro et al., "Extended focused image in microscopy by digital holography." *Optics Express*, vol. 13, No. 18: 6738-6749, 2005.

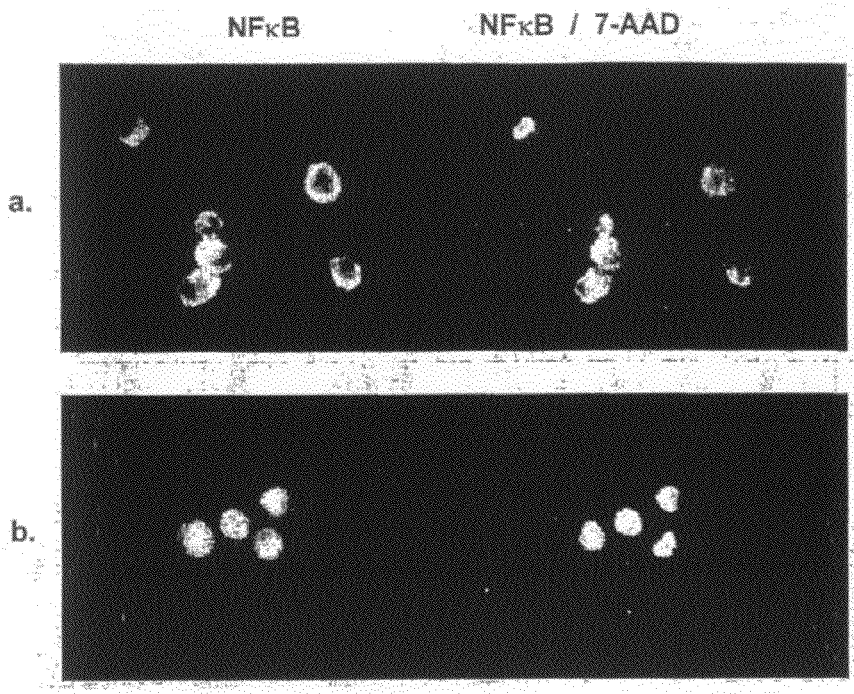

Figure 1: Visualization of NFκB Nuclear Translocation in A549 Cells Using Immunofluorescence Microscopy
TNF-α and IL-1β stimulation initiates a signaling cascade that results in the translocation of NFκB from the cytoplasm to the nucleus of the adherent human carcinoma cell line A549 cells. Untreated A549 cells (a) and A549 cells treated with TNF-α (2 ng/ml) and IL-1β (10 pg/ml) for 1 hour (b) were trypsinized and probed for NFκB expression and nuclear morphology. Briefly, the cells were fixed in 4% paraformaldehyde, permeabilized with 0.1% triton, and incubated with mouse anti-NFκB (p65) + Alexa Fluor® 488 donkey anti-mouse IgG. Cells were washed and resuspended in 1% paraformaldehyde containing 7-AAD, then mixed with an equal volume of antifade and visualized on slides using a Nikon Eclipse E600 fluorescence microscope equipped with bandpass filters appropriate for FITC (535/40 nm) and 7-AAD (630/60 nm) fluorescence. NFκB images in grey are depicted on the left. NFκB (green) / 7-AAD (red) composite images on the right demonstrate the nuclear localization of NFκB following TNF-α / IL-1β treatment.

*Fig. 1*

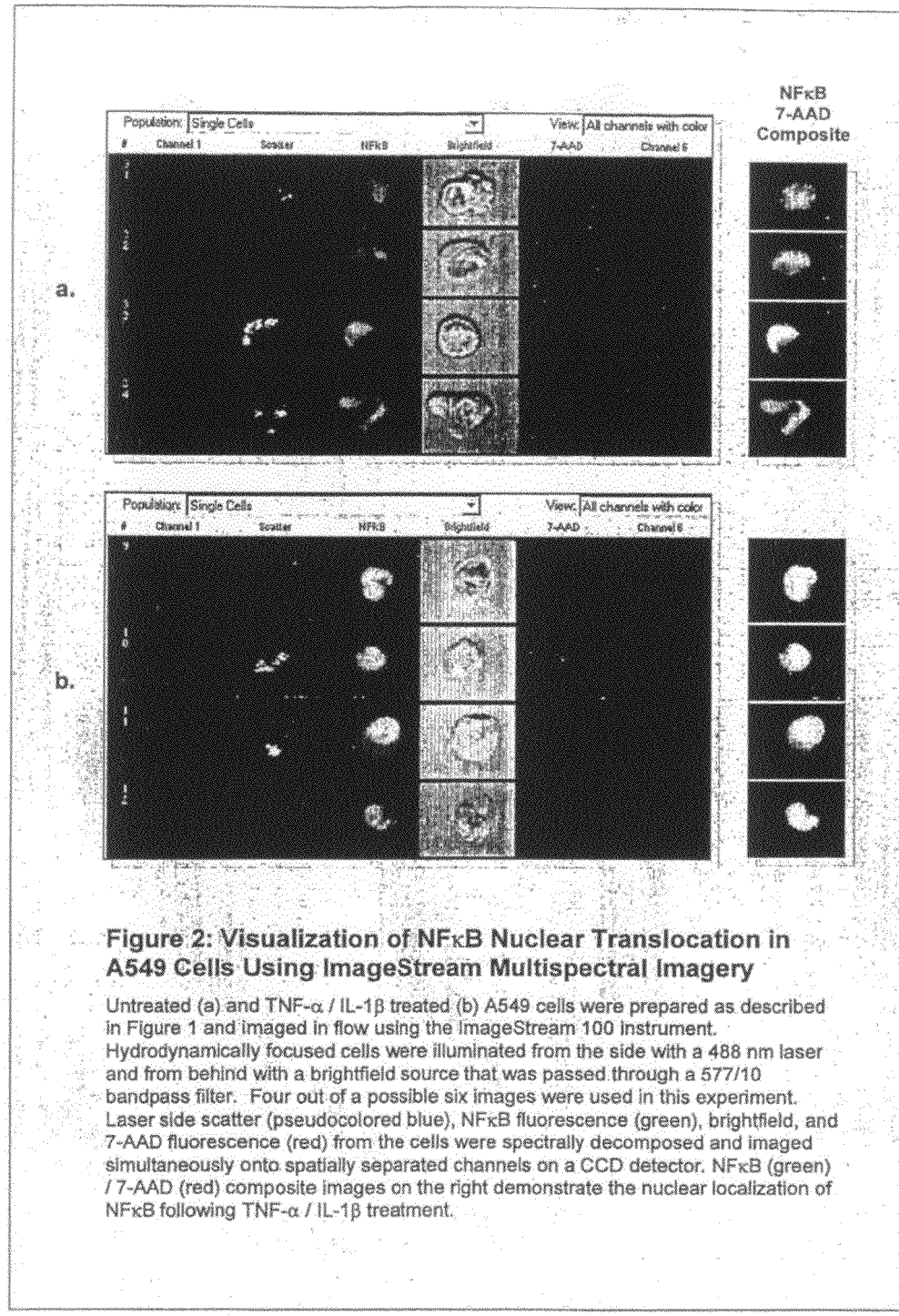

Figure 2: Visualization of NFκB Nuclear Translocation in A549 Cells Using ImageStream Multispectral Imagery Untreated (a) and TNF-α / IL-1β treated (b) A549 cells were prepared as described in Figure 1 and imaged in flow using the ImageStream 100 instrument. Hydrodynamically focused cells were illuminated from the side with a 488 nm laser and from behind with a brightfield source that was passed through a 577/10 bandpass filter. Four out of a possible six images were used in this experiment. Laser side scatter (pseudocolored blue), NFκB fluorescence (green), brightfield, and 7-AAD fluorescence (red) from the cells were spectrally decomposed and imaged simultaneously onto spatially separated channels on a CCD detector. NFκB (green) / 7-AAD (red) composite images on the right demonstrate the nuclear localization of NFκB following TNF-α / IL-1β treatment.

*Fig. 2*

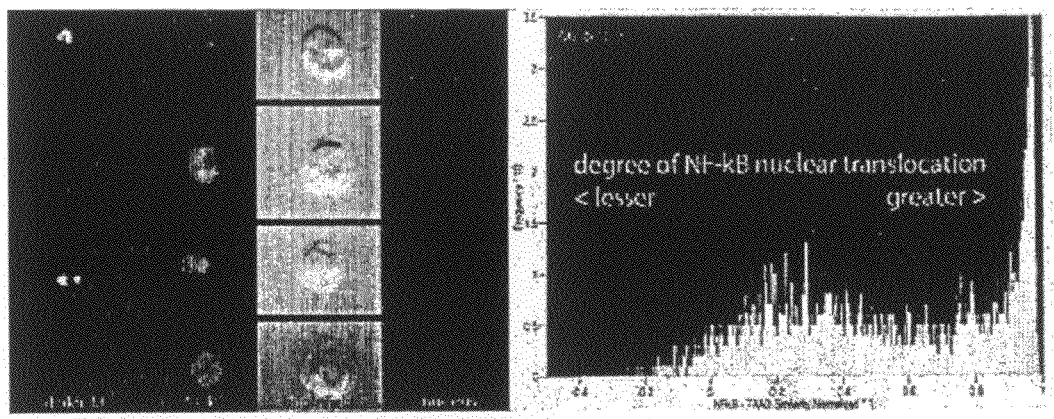

Figure 2C. NF-kB Nuclear Translocation in Immune Cells
The data (above left) show cells imaged simultaneously in darkfield, green fluorescence, brightfield, and red fluorescence. The sample consisted of a monocytic cell line stained with an antibody against the NF-kB transcription factor (green) as well as a nuclear stain (red). Cells treated with lipo-polysaccharide (image rows 2-4) exhibit translocation of NF-kB from the cytoplasm to the nucleus while untreated cells lack NF-kB in the nuclear compartment (top row). A statistical analysis of imagery from 6616 cells quantitatively characterizes the degree of NF-kB nuclear translocation in the sample. Amnis' ImageStream platform is the only cell analysis technology that can perform this valuable assay on immune cells in suspension.

*Fig. 2C*

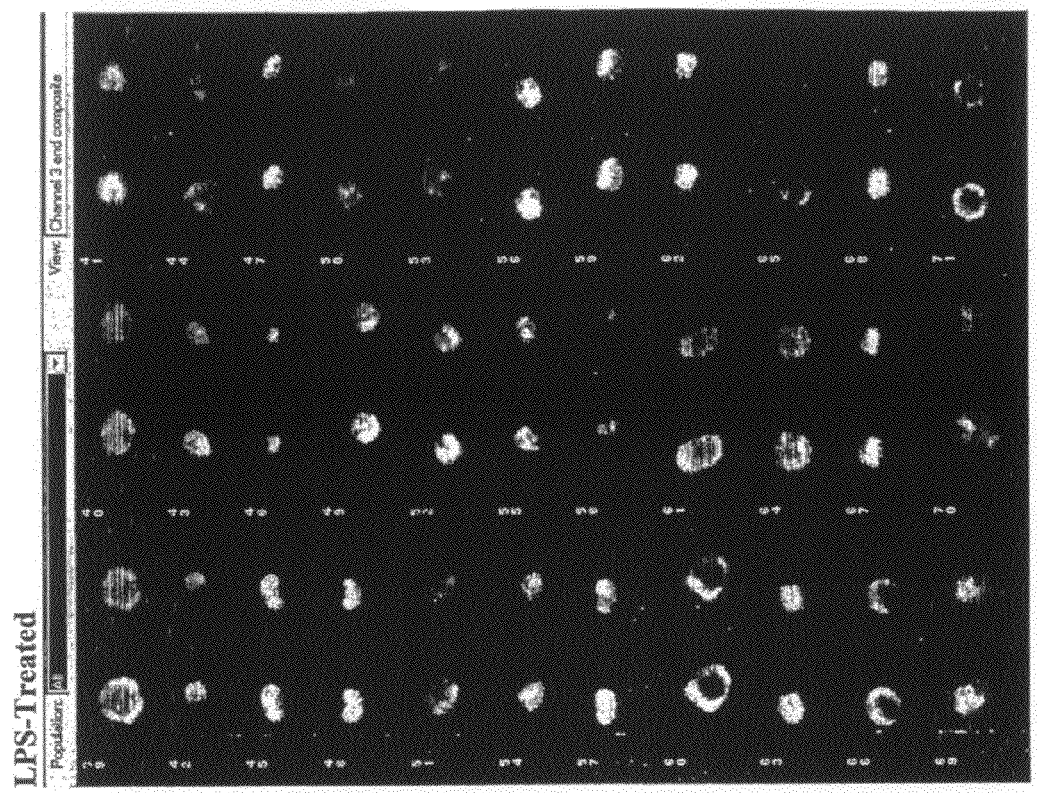
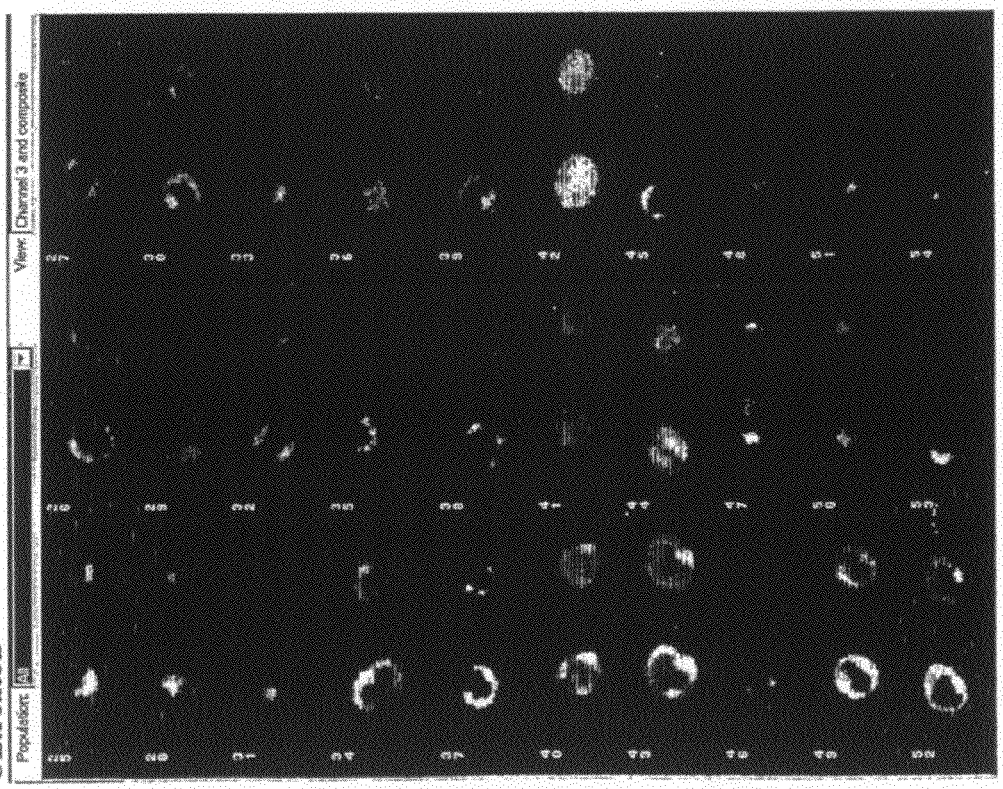
Fig. 7

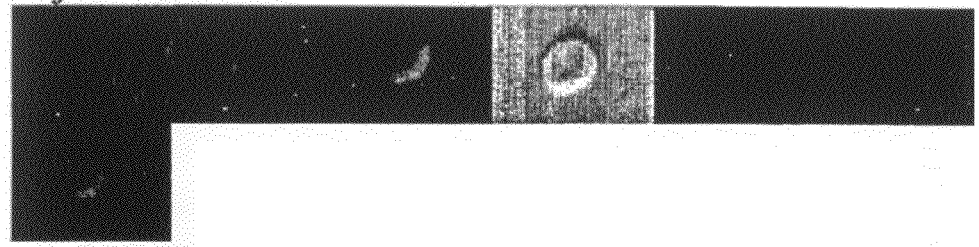
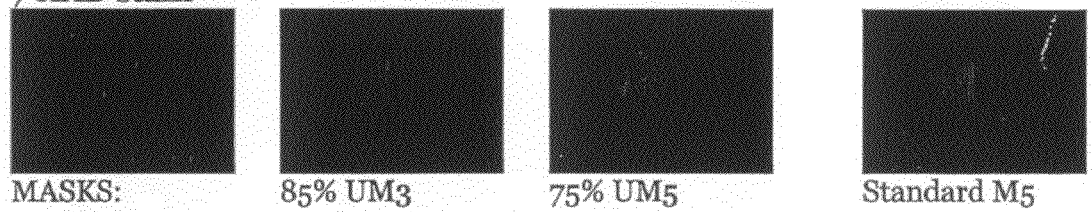
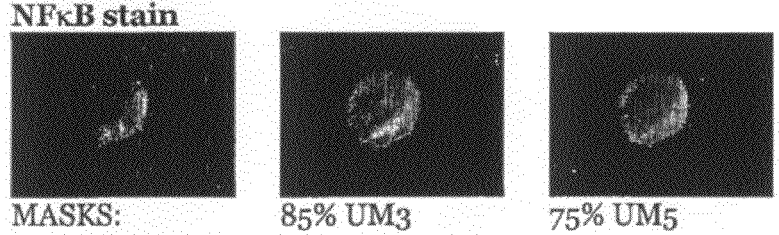
*Fig. 8*

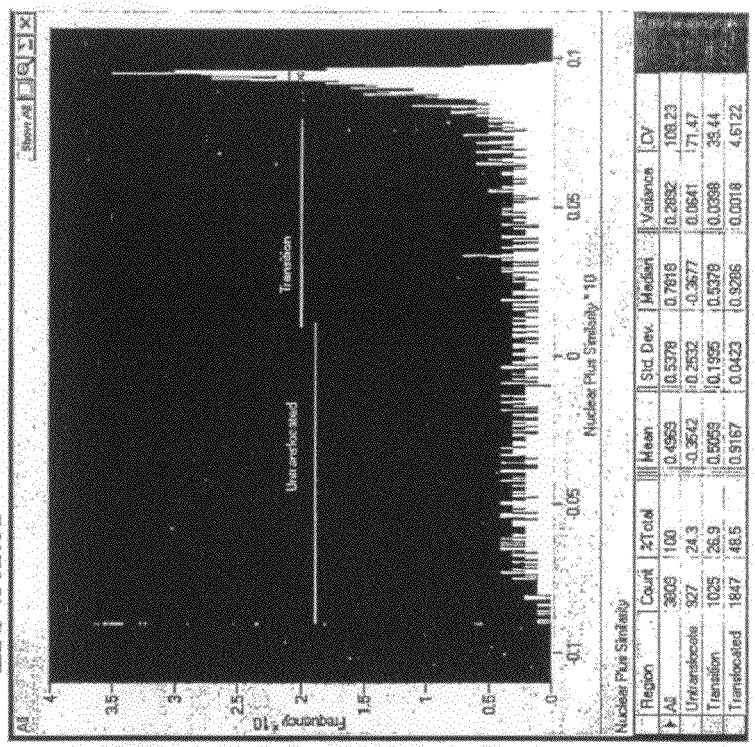
COMPARTMENTAL CORRELATION FEATURE:
Untreated / LPS-treated
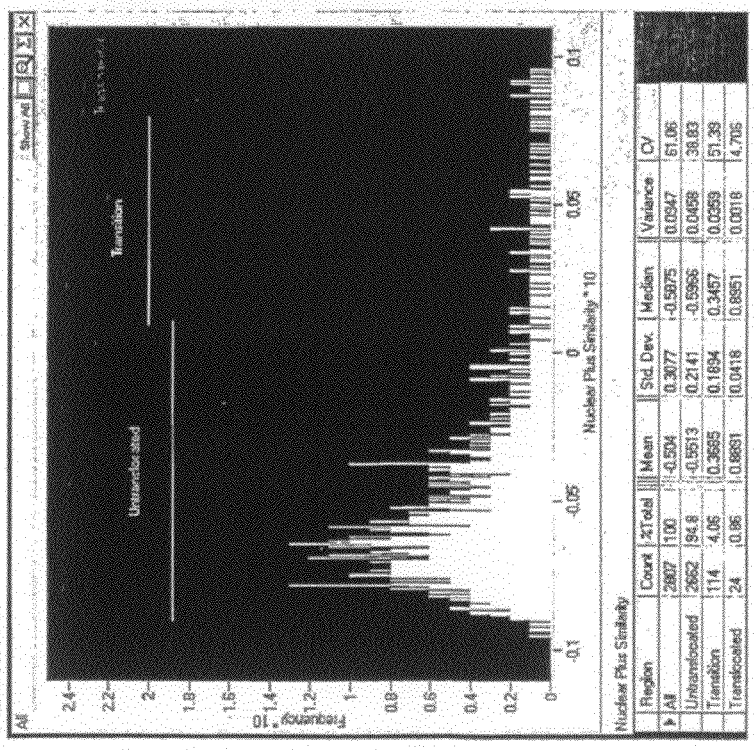
Median Compartmental Corelation Feature:
Untranslocated = -0.5966 +/- 0.2141
Translocated = 0.9286 +/- 0.0423
Difference of 1.5252
*Fig. 9*

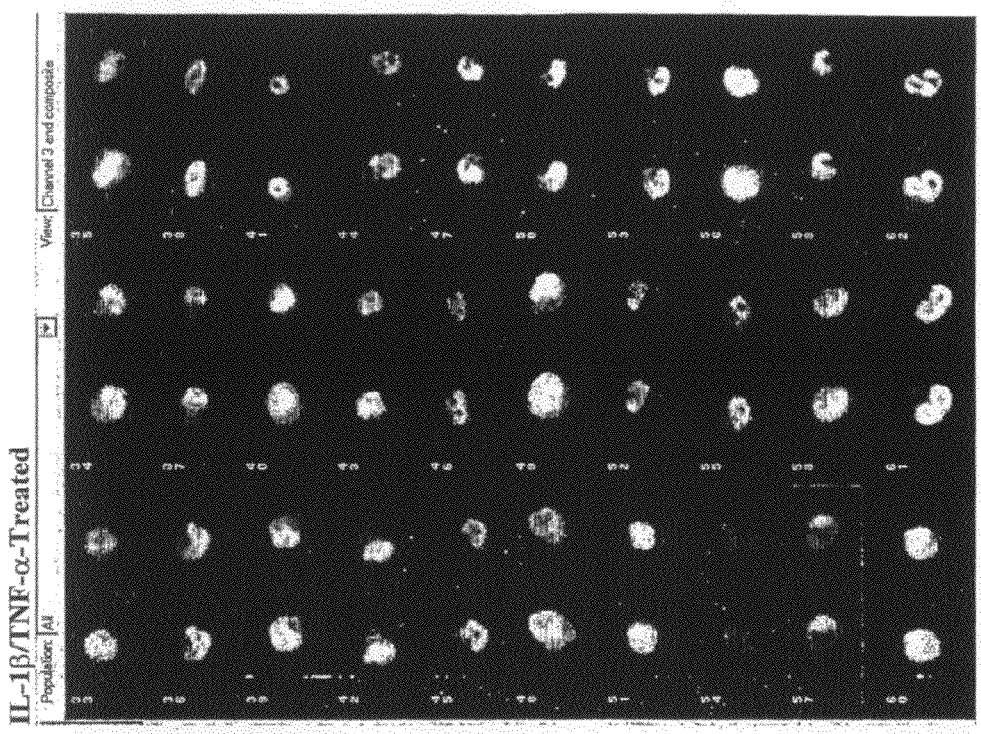
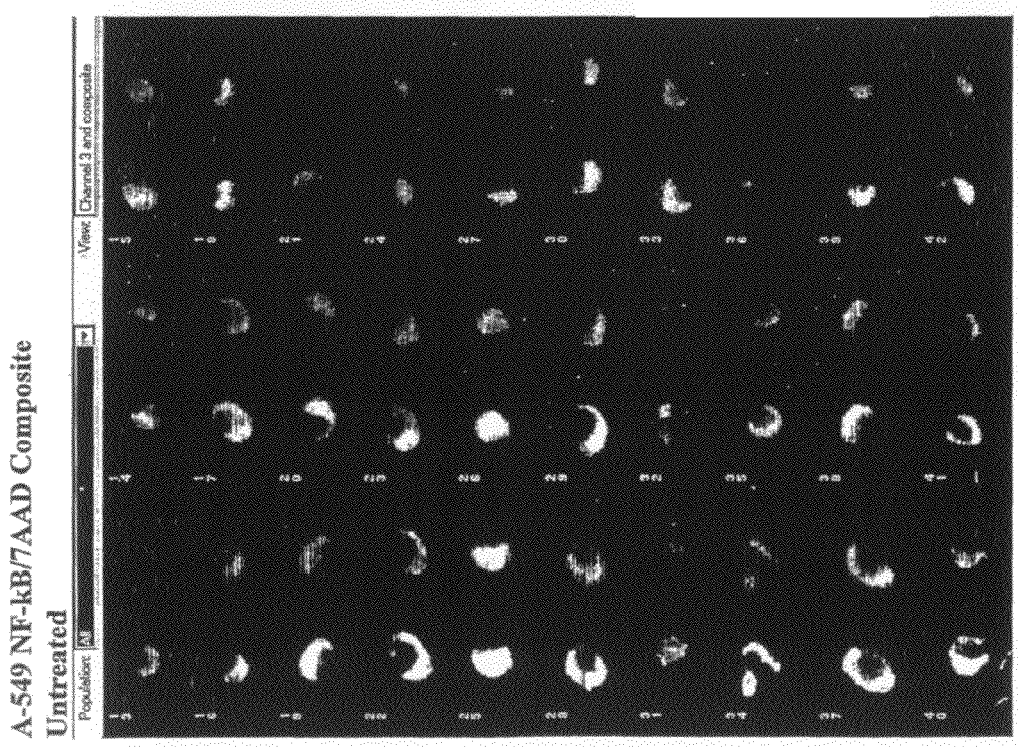
Fig. 12

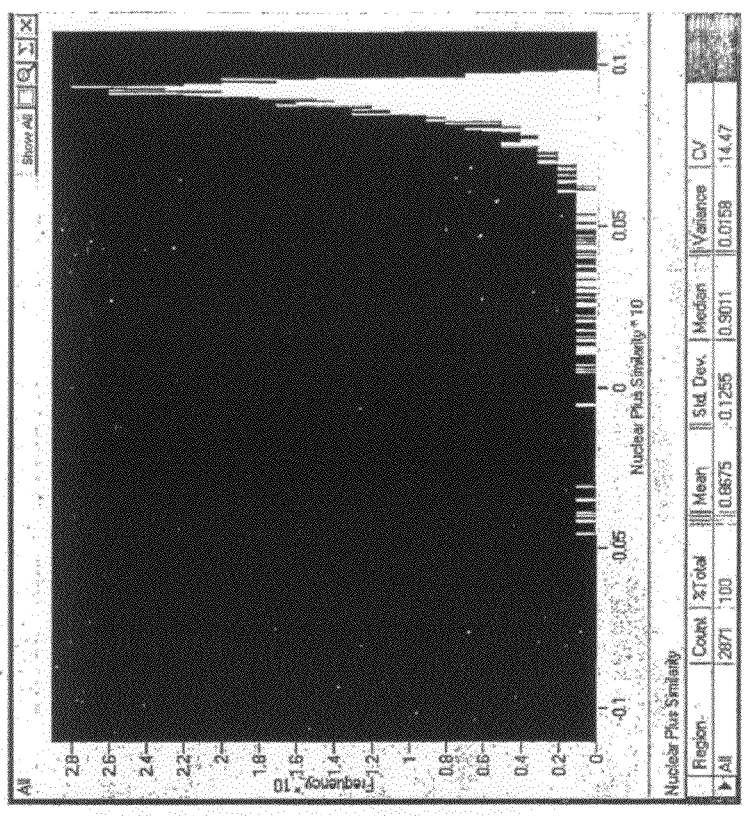
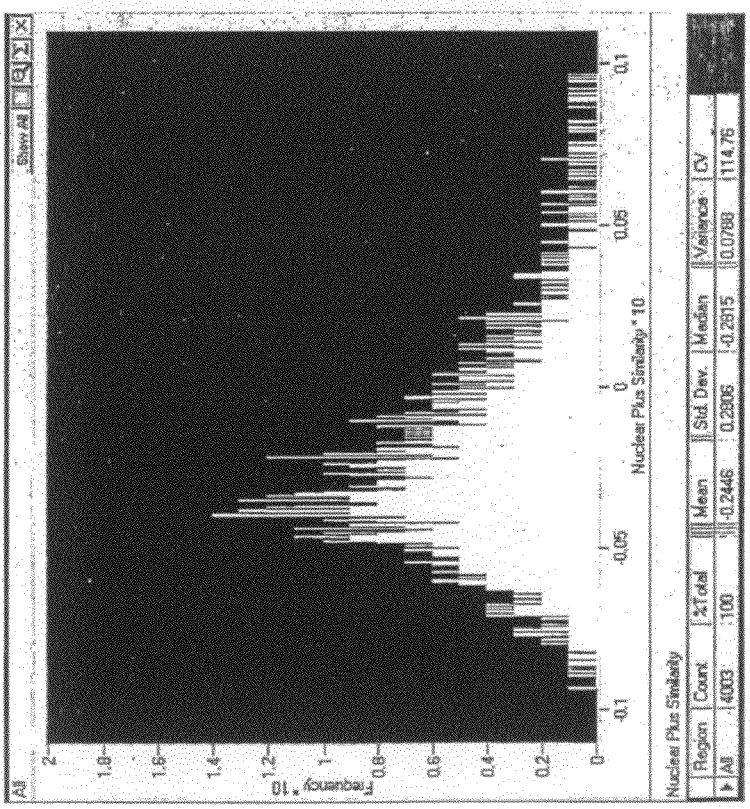
Fig. 13

IMAGE BASED QUANTITATION OF MOLECULAR TRANSLOCATION

BACKGROUND OF THE INVENTION

1. Field of the Invention

The present disclosure relates generally to methods for detecting specific molecules in cells, and more specifically, to the use of imagery in methods for quantitating the movement of molecules within a cell, including adherent and non-adherent cells, such as movement to the nucleus, or to another cellular organelle or compartment.

2. Description of the Related Art

Signal transduction pathways regulate most cellular biological processes and have a critical influence on cellular responses to external stimuli. Typically, cell surface receptors that bind to a specific extracellular mediator trigger a cascade of intracellular signaling events that alter cellular metabolism or gene expression, and such changes contribute to the cellular response. The intracellular signaling cascade often involves the translocation of transcription factors or second messengers from the cytoplasm to the nucleus.

Historically, nuclear translocation events have been studied microscopically by observing the sub-cellular localization of fluorescent probe-labeled signaling molecules. Until recently, microscopic applications have been limited due to the subjective nature and the lack of means to quantitate imagery. Currently, several quantitative plate based microscopy platforms are available that attempt to quantitate translocation (ArrayScan, Cellomics, Inc. (Pittsburgh, Pa.); Laser Scanning Cytometer, Compucyte Corporation (Cambridge, Mass.); IN Cell Analyzer, Amersham International plc. (Little Chalfont, England)). However, these microscopy platforms typically rely on the use of adherent cell lines, and their biological responses may differ from suspension-type cells (which include most blood cells).

Traditionally, the measurement of the translocation of fluorescently bound molecules into the nucleus has been determined by a method referred to as the Nuc-Cyt difference (Ding et al., *J. Biol. Chem.* 273:28897, 1998). This measurement involves the following steps: (1) determining the boundaries of the nucleus which has been stained with a nuclear stain; (2) eroding the mask or area contained with in the boundaries to insure the entire area is within the nucleus; (3) summing up the total fluorescence intensity associated from the labeled molecules of interest (Total Nuclear Fluorescence); (4) dilating the nuclear boundary to determine an annular ring solely contained in the cytoplasm and integrate the fluorescence associated with the labeled molecule of interest (Annular Cytoplasm Fluorescence); and (5) calculating the difference between the Total Nuclear and Annular Cytoplasm Fluorescence to yield the Nuc-Cyt difference. However, this method is unlikely to produce the best measurement because it relies on an accurate nuclear mask, subjective erosion and dilation routines that determine the nuclear and cytoplasmic boundaries, an additional subjective dilation of the cytoplasm mask to create an annular volume, and both the cytoplasm and the nucleus have areas that are not represented in the calculation.

Thus, the need exists for techniques that can allow quantitation of molecular transport, such as nuclear translocation, in cells in flow to afford the opportunity to study suspension-based cell lines as well as primary cells. For example, such techniques would allow detailed analysis of nuclear translocation responses in subset of cells, such as blood cells. The present invention meets such needs, and further provides other related advantage.

BRIEF DESCRIPTION OF THE DRAWINGS

FIG. 1 shows staining of NFκB nuclear translocation in A-549 cells using immunofluorescence microscopy.

FIGS. 2A and 2B show staining of NFκB nuclear translocation in A-549 cells using multispectral imaging.

FIG. 2C shows staining of nuclear translocation of NF-κB in immune cells. The left panel shows a monocytic cell line imaged simultaneously in darkfield, green fluorescence (fluorescein isothiocyanate (FITC) labeled anti-NF-κB), brightfield, and red fluorescence (nuclear stain 7-aminoactinomycin D). Each image row represents a different, single cell. The first cell is untreated and cells 2-4 have been treated with lipopolysaccharide (LPS). The right panel is a statistical analysis of the imagery that quantitatively characterizes the degree of NF-κB translocation to the nucleus.

FIG. 7 shows images of nuclear translocation of NF-κB in THP-1 cells untreated (left panel) and treated with LPS (right panel). Images include brightfield and a composite of cells stained with anti-NF-κB and with 7-AAD.

FIG. 8 shows 7-AAD mask and NF-κB mask used in a compartmental correlation feature calculation.

FIG. 9 shows quantitation of compartmental correlation feature in untreated and LPS-treated THP-1 cells.

FIG. 12 shows images of nuclear translocation of NF-κB in A-549 cells untreated (left panel) and treated with IL-1β/TNF-α (right panel). Images include brightfield and a composite of cells stained with anti-NF-κB and with 7-AAD.

FIG. 13 shows quantitation of compartmental correlation feature in untreated and IL-1β/TNF-α-treated A-549 cells.

DETAILED DESCRIPTION

Figure 3:
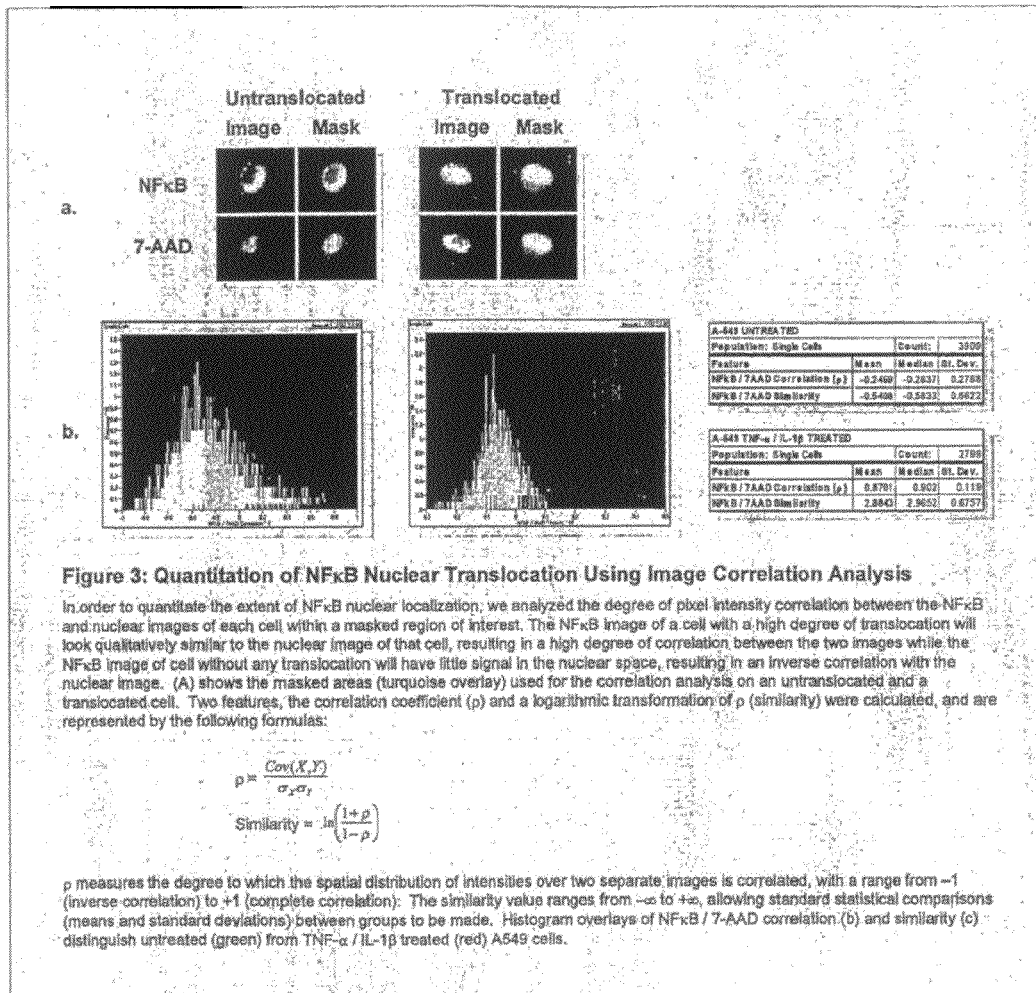
FIG. 3 shows quantitation of NFκB nuclear translocation in A-549 cells using image correlation analysis (see FIG. 3 for more detail).
Figure 4:
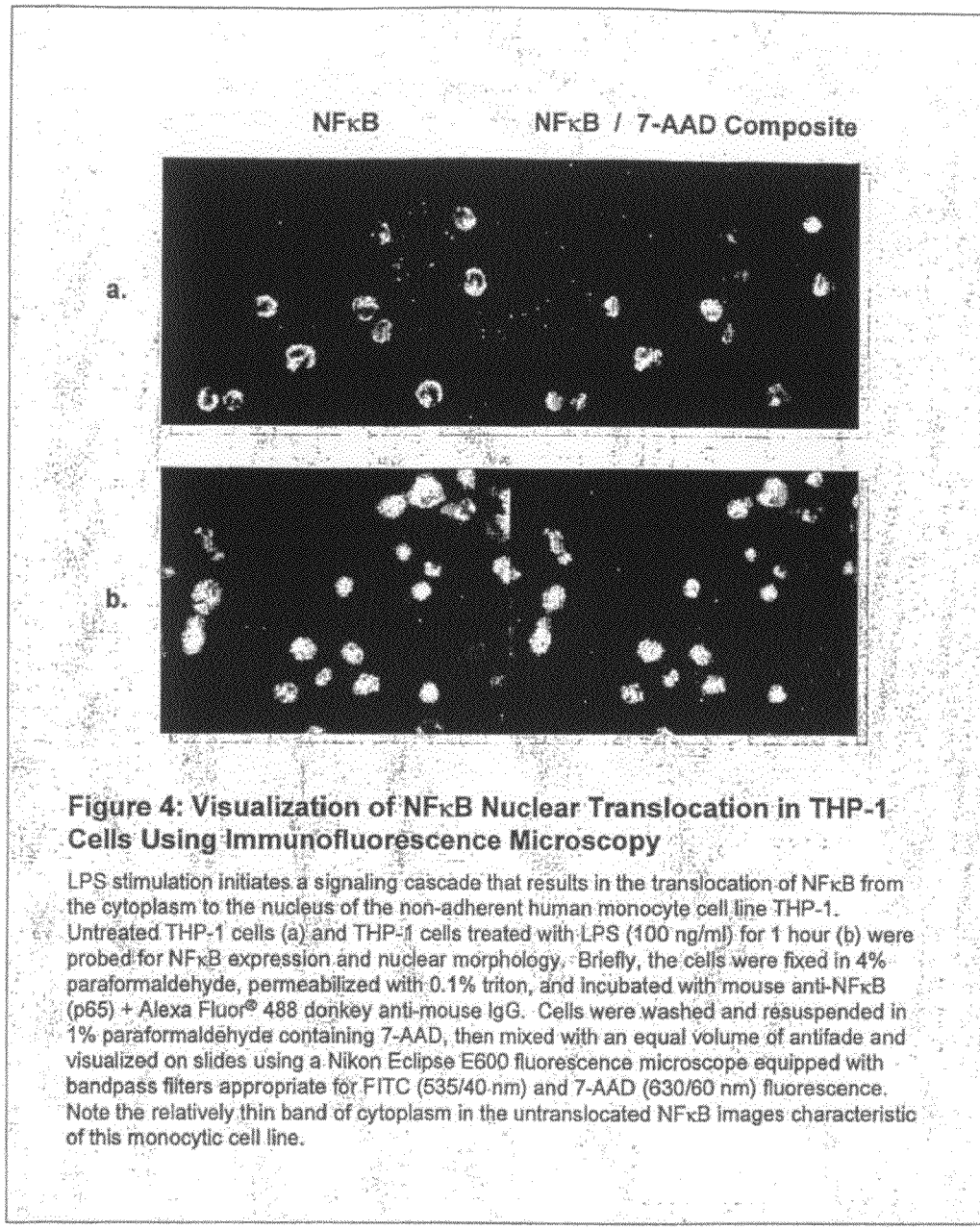
FIG. 4 shows staining of NFκB nuclear translocation in THP-1 cells using immunofluorescence microscopy.
Figure 5:
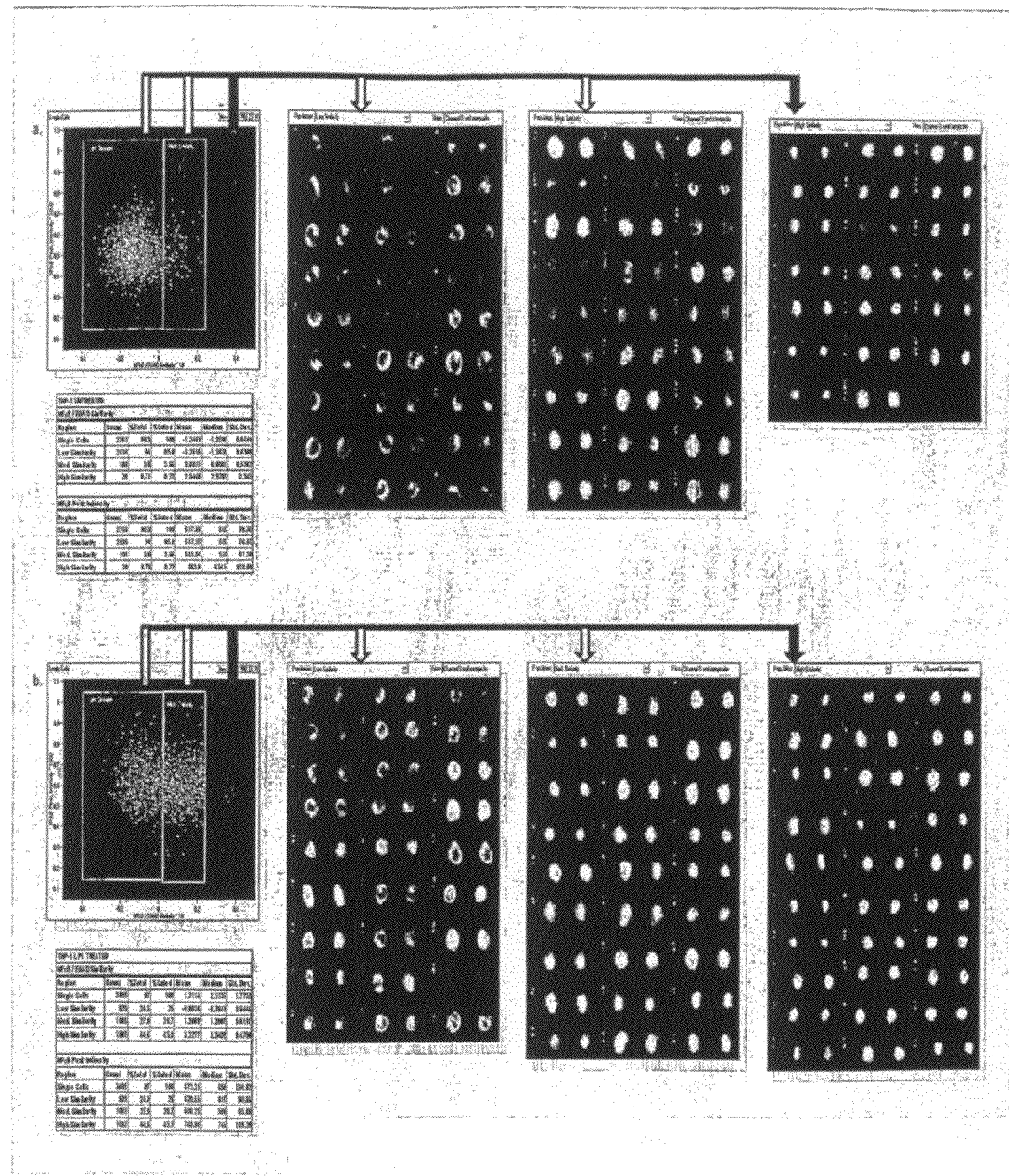
FIG. 5 shows staining and quantitation of NFκB nuclear translocation in THP-1 cells using multispectral imaging. Untreated (a) and LPS treated (b) THP-1 cells were prepared as described in FIG. 4 and imaged in flow using the ImageStream 100 platform. Plotting NF-κB/7-AAD Similarity vs. NF-κB Peak Intensity revealed a range of cells based on similarity that were gated into three populations. Each gated population has an associated image gallery that can be visually inspected. The image galleries here display the NF-κB image adjacent to a composite image (green NF-κB/red 7-ADD) for each object within a given population. Morphologic inspection of the image galleries revealed that NF-κB had translocated to the nucleus in 'High Similarity' but not 'Low Similarity' cells. 'Medium Similarity' cells had a diffuse NF-κB staining pattern. Untranslocated and translocated cells had significantly different Similarity values (untreated: −1.36 +/−0.84 and 2.98 +/−0.35, respectively; LPS treated: −0.76 +/−0.64 and 3.35 +/−0.48, respectively). Treatment with LPS significantly increased the percentage of NF-κB-translocated (0.71%, median similarity value 2.98 +/−0.35 to 44.6%, median similarity value 3.35 +/−0.48) and Medium Similarity (3.6% to 27.6%) cells.

The instant disclosure relates to the use of multi-mode imagery of cells, including in non-adherent and adherent cell types, to monitor or identify molecular processes and movement in and between all cellular compartments. An advantage of the methods provided in the instant disclosure is that the shortcomings of the Nuc-Cyt difference calculation discussed above are generally obviated. Specifically, the methods of the instant disclosure use a measurement based upon statistical correlation, referred to herein as Compartmental Correlation Feature (CCF), which is a more robust method than the Nuc-Cyt calculation because (i) a single Nuclear Mask is used, (ii) spatial information is taken into account, (iii) subjective dilation, erosion, and annular dilation routines are not required, and (iv) the entire cellular nucleus is taken into account. Discussed in more detail below are single-step methods of using morphometric and photometric features from comprehensive multispectral imagery, in combination with CCF, to permit the analysis or observation of, for example, molecular movement or transport into a cell, out of a cell, within a cell, or between subcellular compartments. Thus, it should be understood that reference herein to "movement of a molecule in a cell" encompasses movement or transport of a molecule or molecules into a cell, out of a cell, within a cell, or between subcellular compartments, and combinations thereof. An exemplary image system for use with the methods in the instant disclosure is an ImageStream® 100 multispectral imaging flow cytometer platform, which produces high-resolution brightfield, darkfield, and fluorescence images with the simplified sample handling and quantitative power of flow cytometry. In addition, the IDEAS™ analysis software can quantify over 200 photometric and morphometric parameters for each cell that passes through the imaging system, including parameters that can quantify the cellular and sub-cellular location of molecules, probes, and other indigenous or exogenous compounds within a cell.

In the present description, any concentration range, percentage range, ratio range, or integer range is to be understood to include the value of any integer within the recited range and, when appropriate, fractions thereof (such as one tenth and one hundredth of an integer, etc.), unless otherwise indicated. As used herein, the term "about" means ±15%. As used herein, the use of an indefinite article, such as "a" or "an", should be understood to refer to the singular and the plural of a noun or noun phrase (i.e., meaning "one or more" of the enumerated elements or components). The use of the alternative (e.g., "or") should be understood to mean either one, both or any combination thereof of the alternatives.

By way of background, methodologies for simultaneous high speed multispectral imaging in brightfield, darkfield, and four channels of fluorescence of cells in flow were recently developed (see, e.g., U.S. Pat. Nos. 6,211,955 and 6,249,341). U.S. Patent Application No. 2002/0146734 illustrates an exemplary imaging system (e.g., the ImageStream platform). Cells are hydrodynamically focused into a core stream and orthogonally illuminated for both darkfield and fluorescence imaging. The cells are simultaneously trans-illuminated via a spectrally-limited source (e.g., filtered white light or a light emitting diode) for brightfield imaging. Light is collected from the cells with an imaging objective lens and is projected on a charge-coupled detector (CCD). The optical system has a numeric aperture of 0.75 and the CCD pixel size in object space is 0.5 microns square, allowing high resolution imaging at event rates of approximately 100 cells per second. Each pixel is digitized with 10 bits of intensity resolution, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object.

Prior to projection on the CCD, the light is passed through a spectral decomposition optical system that directs different spectral bands to different lateral positions across the detector (see, e.g., U.S. Pat. No. 6,249,341). With this technique, an image is optically decomposed into a set of 6 sub-images, each corresponding to a different color component and spatially isolated from the remaining sub-images. This process allows for identification and quantitation of signals within the cell by physically separating on the detector signals that may originate from overlapping regions of the cell. Spectral decomposition also allows multimode imaging: the simultaneous detection of brightfield, darkfield, and multiple colors of fluorescence. This is exemplified in the figures of U.S. Patent Application No. 2002/0146734, which depicts a red brightfield illumination source and the associated transmitted light images in the red detector channel adjacent to fluorescent and scattered light images in the other spectral channels. The process of spectral decomposition occurs during the image formation process rather than via digital image processing of a conventional composite image.

The CCD may be operated using a technique called time-delay-integration (TDI), a specialized detector readout mode that preserves sensitivity and image quality even with fast relative movement between the detector and the objects being imaged. As with any CCD, image photons are converted to photocharges in an array of pixels. However, in TDI operation the photocharges are continuously shifted from pixel to pixel down the detector, parallel to the axis of flow. If the photocharge shift rate is synchronized with the velocity of the flowing cell's image, the effect is similar to physically panning a camera: image streaking is avoided despite signal integration times that are orders of magnitude longer than in conventional flow cytometry. For example, an instrument may operate at a continuous data rate of approximately 30 megapixels per second and integrate signals from each object for 10 milliseconds, allowing the detection of even faint fluorescent probes within cell images that are acquired at high-speed. Careful attention to pump and fluidic system design to achieve highly laminar, non-pulsatile flow eliminates any cell rotation or lateral translation on the time scale of the imaging process (see, e.g., U.S. Pat. No. 6, 532,061).

A real-time algorithm analyzes every pixel read from the CCD to detect the presence of object images and calculate a number of basic morphometric and photometric features, which can be used as criteria for data storage. Data files encompassing 10,000-20,000 cells are typically about 100 MB in size and, therefore, can be stored and analyzed using standard personal computers. The TDI readout process operates continuously without any "dead time", which means every cell can be imaged and the coincidental imaging of two or more cells at a time presents no barrier to data acquisition.

Such an imaging system can be employed to determine morphological, photometric, and spectral characteristics of cells and other objects by measuring optical signals, including light scatter, reflection, absorption, fluorescence, phosphorescence, luminescence, etc.

As used herein, "morphological parameters" may be basic (e.g., nuclear shape) or may be complex (e.g., identifying cytoplasm size as the difference between cell size and nuclear size). For example, morphological parameters may include nuclear area, perimeter, texture or spatial frequency content, centroid position, shape (i.e., round, elliptical, barbell-shaped, etc.), volume, and ratios of any of these parameters. Morphological parameters may also include cytoplasm size, texture or spatial frequency content, volume and the like, of cells. Morphological parameters may also be of other organelles (e.g., mitochondria) or for other cellular compartments (e.g., plasma membrane or organelle membrane).

As used herein, "photometric measurements" with the aforementioned imaging system can enable the determination of nuclear optical density, cytoplasm optical density, background optical density, and the ratios of any of these values. An object being imaged can be stimulated into fluorescence or phosphorescence to emit light, or may be luminescent wherein light is produced without stimulation. In each case, the light from the object may be imaged on a TDI detector of the imaging system to determine the presence and amplitude of the emitted light, the number of discrete positions in a cell or other object from which the light signal(s) originate(s), the relative placement of the signal sources, and the color (wavelength or waveband) of the light emitted at each position in the object.

In using an imaging system as described herein, it should be made clear that a separate light source is not required to produce an image of the object (cell), if the object is luminescent (i.e., if the object produces light). However, many of the applications of an imaging system as described herein will require that one or more light sources be used to provide light that is incident on the object being imaged. A person having ordinary skill in the art will know that the location of the light sources substantially affects the interaction of the incident light with the object and the kind of information that can be obtained from the images on a TDI detector.

In addition to imaging an object with the light that is incident on it, a light source can also be used to stimulate emission of light from the object. For example, a cell having been contacted with probe conjugated to a fluorochrome (e.g., such as FITC, PE, APC, Cy5, or Cy5.5) will fluoresce when excited by light, producing a corresponding characteristic emission spectra from any excited fluorochrome probe that can be imaged on a TDI detector. Light sources may alternatively be used for causing the excitation of fluorochrome probes on an object, enabling a TDI detector to image fluorescent spots produced by the probes on the TDI detector at different locations as a result of the spectral dispersion of the light from the object that is provided by prism. The disposition of these fluorescent spots on the TDI detector surface will depend upon their emission spectra and their location in the object.

Each light source may produce light, which can either be coherent, non-coherent, broadband or narrowband light, depending upon the application of the imaging system desired. Thus, a tungsten filament light source can be used for applications in which a narrowband light source is not required. For applications such as stimulating the emission of fluorescence from probes, narrowband laser light is preferred, since it also enables a spectrally decomposed, non-distorted image of the object to be produced from light scattered by the object. This scattered light image will be separately resolved from the fluorescent spots produced on a TDI detector, so long as the emission spectra of any of the spots are at different wavelengths than the wavelength of the laser light. The light source can be either of the continuous wave (CW) or pulsed type, preferably a pulsed laser. If a pulsed type illumination source is employed, the extended integration period associated with TDI detection can allow the integration of signal from multiple pulses. Furthermore, it is not necessary for the light to be pulsed in synchronization with the TDI detector.

The present disclosure provides methods of using both photometric and morphometric features derived from multi-mode imagery of objects in flow. Such methods can be employed to analyze molecular movement within or between cells, in heterogeneous populations of cells when entrained in a fluid flowing through an imaging system. As used herein, cells may be eukaryotic or prokaryotic or viral, human, non-human animal, plant, unicellular, a primary cell culture or culture-adapted cell line, immortalized or immortalizable, differentiated or differentiatable, and the like. In addition, cells may be genetically engineered (transduced, transformed or transfected) with one or more chromosomally integrated or episomal recombinant nucleic acid sequences. The cells may have been exposed to one or more chemicals or compounds to induce or repress signaling pathways (e.g., signal transduction pathway) or other cellular function. However, it should be understood that these cells and exemplary methods might be used for imaging and distinguishing other moving objects that have identifiable photometric and morphometric features, such as systems biology structures (cytomic objects), organelles, liposomes, subcellular compartments, polymeric microspheres or capsules, nanostructures, nanomolecules, and the like.

In the embodiments of the present invention, it is to be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion, which movement may be in different directions and/or at different rates.

In any of the aforementioned methods, multiple images may be collected simultaneously. Furthermore, in any of the aforementioned methods, there is relative motion between the cell and the detector. In addition, in any of the aforementioned methods, the detector is a time delay integration charge-coupled detector.

Compartmental Correlation Feature

As set forth above, the methods of the instant disclosure have been designed to overcome the shortcomings of the Nuc-Cyt difference calculation when monitoring, for example, nuclear translocation. That is, the Nuc-Cyt calculation requires, among other routines, accurate determination of a nuclear mask, subjective erosion and dilation routines that determine the nuclear and cytoplasmic boundaries, and subjective dilation of the cytoplasm mask to create an annular volume. The instant disclosure provides the use of an imaging system to track or correlate the movement of a molecule in a cell using a calculation referred to as Compartmental Correlation Feature (CCF). For example, using the multispectral imaging capabilities of an imaging system (e.g., ImageStream®), at least two different spectral images are collected corresponding to the emission wavelengths of a fluorescent dye specific for a cellular compartment (e.g., nucleus, mitochondria, cytoplasm, membrane) and a fluorescent dye specific for a translocated molecule. A cellular compartment mask may be generated based on the cellular compartment stain image, then a correlation measurement is made between the cellular compartment mask and the dye area of the translocated molecule. Consequently, molecules that are translocated to the targeted cellular compartment should have a high correlation (i.e., the images should show significant overlap), whereas cells lacking cellular compartment translocation should have a low correlation (i.e., images that show less of an overlap). The correlation value for each cell can be plotted as a histogram, which will display the degree of cellular compartment translocation of a molecule for a cell population. Furthermore, as noted above, the CCF can be used to determine or analyze molecular movement within any cellular compartment, such as translocation to or from the nucleus, movement to or from the cytoplasm, or movement to or from a cellular membrane, etc., and combinations thereof.

FIG. 2 illustrates the case of a nuclear translocation assay in which a fluorescent nucleic acid binding dye, 7-aminoactinomycin D (7-AAD, shown as red fluorescence), is used to stain the nucleus, while a different fluorescent marker (green; e.g., a FITC conjugated antibody) is used to label a translocating molecule of interest (e.g., NF-κB). Using the multispectral imaging capabilities of, for example, the ImageStream®, at least two different spectral images are collected, corresponding to the emission wavelengths of the nuclear fluorescent dye and the fluorescent dye on the molecule NF-κB (to track translocation). A nuclear mask is generated from the nuclear stain image and then a correlation measurement is made between the nuclear mask area of both fluorescence channels. Cells that exhibited nuclear translocation of NF-κB had a high correlation (see, e.g., FIG. 2C, image rows 2-4), while cells with low nuclear translocation had a low correlation (see, e.g., FIG. 2C, image row 1). The correlation value for each cell was plotted as a histogram, which displays the degree of NF-κB nuclear translocation for the cell population (see, e.g., FIG. 2C, graph on right).

Compartmental Correlation Feature Calculation

Compartmental Correlation is a measurement based upon a statistical definition of correlation. The correlation of X and Y is the measurement defined by $$\rho(X,Y)=\text{Cov}(X,Y)/(\sigma_X \sigma_Y)$$

in which X and Y are the fluorescent nuclear and translocating molecule. images.

Cov(X,Y) is the covariance of X and Y and is defined by:
Cov(X,Y)=Expected Value of $[(X-\mu_X)(Y-\mu_Y)]$
Also, $\mu_X, \sigma_X$ and $\mu_Y, \sigma_Y$ are the mean and standard deviations of X and Y, respectively. The measurement $\rho(X,Y)$ is also known as the correlation coefficient. Correlation is most effective in measuring relationships between X and Y that are linear.

Similarity can be correlation, which is applied to imagery wherein X and Y are the pixel representations of imagery. First, the mask, M, is defined, wherein M is the set of coordinates (i,j). Then N can equal the number of elements in the set M. Then:

$$\mu X = \Sigma X(i,j)/N \text{ and } \sigma_X = \text{sqrt}\{\Sigma(X(i,j)-\mu_X)(X(i,j)-\mu_X))/(N-1)\},$$

$$\mu Y = \Sigma Y(i,j)/N \text{ and } \sigma_X = \text{sqrt}\{\Sigma(Y(i,j)-\mu_Y)(Y(i,j)-\mu_Y))/(N-1)\},$$

$$\text{Cov}(X,Y) = \Sigma(X(i,j)-\mu X)(Y(i,j)-\mu_Y))/(N-1)$$

When Compartmental Correlation is applied to images that exhibit molecular movement or translocation, this value tends to shift closer to a value of 1.0. When the images reveal lack of molecular movement or translocation (untranslocation), this value tends to shift closer to a value of −1.0. The Compartmental Correlation measurement and the imagery indicate that the different degree of translocation of NFκB into the nucleus is a linear relationship. Therefore, Compartmental Correlation is optimal for measuring such a relationship.

An exemplary embodiment of such a correlation is shown in FIG. 3. In order to quantitate the extent of NF-κB nuclear translocation in A-549 cells treated with TNF-α/IL-β, the degree of pixel intensity between the NF-κB and nuclear images of cell within a masked region of interest was analyzed. The NF-κB image of a cell with a high degree of translocation will look qualitatively similar to the nuclear image of that cell, resulting in a high degree of correlation between the two images. In contrast, the NF-κB image of a cell without any translocation will have little signal in the nuclear space, resulting in an inverse correlation with the nuclear image. FIG. 3A shows the masked areas used for the correlation analysis on an untranslocated and a translocated cell. Two features were calculated, the correlation coefficient (ρ) and, in this case, similarity is calculated as a logarithmic transformation of ρ, which features are represented by the following formula, respectively:

$$\rho(X,Y)=\text{Cov}(X,Y)/(\sigma_X \sigma_Y)$$

$$\text{Similarity}=\ln(1+\rho)/(1-\rho)$$

As set forth herein, ρ measures the degree to which the spatial distribution of intensities over two separate images is correlated, with a range from −1 (inverse correlation) to +1 (complete correlation). Here, similarity values range from −∞ to +∞, allowing standard statistical comparisons (means and standard deviations) between groups to be made. Histogram overlays of NF-κB/7-AAD correlation and similarity allows the differentiation of untreated (green) A-549 cells from TNF-α/IL-1β treated (red) A-549 cells. As described herein, the fidelity of these classifiers can be validated by inspection of the image galleries of the cells.

Mask Determination

In order for the correlation between pixel intensities to provide unambiguous evidence for or against the co-location of probes (e.g., labeled molecules) in cells, an appropriate sub-set of pixels should be selected over which the correlation is to be computed. If, for example, background pixels not belonging to the cell of interest are included in the set, a strong positive correlation may be found, even when the probes tend to separate within the cell because both probes are present in larger quantities within the cell than outside the cell. In general, a variety of chemical, morphological, and intensity-based methods may need to be applied in a given experiment to select the pixels of interest.

In the example of nuclear translocation, the task of selecting the pixels of interest is simplified by the presence of the nuclear probe. In this assay, the pixels of interest are those directly illuminated by the nucleus and cytoplasm. The presence of the nuclear probe means that all that is usually needed to get a sufficiently accurate set of pixels is a mask based on a blurred image of the nuclear probe, perhaps extended to include regions (near the nucleus) where the nuclear probe intensity is varying sufficiently rapidly. In the case of membrane probes, certain parameters should be chosen, such as a narrow band of pixels right on the edge of the cell, while excluding from consideration those either on the interior or exterior. Morphological criteria will play a role in constructing an appropriate set of pixels in the case of membranes and the morphology required is of two types. The first is a local constraint, requiring the band of pixels of increased intensity to be sufficiently narrow in order to qualify as a piece of the membrane. The second is a more global criterion, requiring that the band of pixels be sufficiently close to the global boundary defining the interior of the cell.

Uses

A multispectral imaging system and CCF can be used in a variety of applications, including diagnostics, drug discovery, and the like. For example, an imaging system may be used to identify compounds that affect or alter the activation of transcription factor NF-κB in cells of the immune system. Immune cells may be contacted with particular chemicals, cytokines, or environmental agents to examine whether translocation of the NF-κB molecule from the cytoplasm to the nucleus occurs as part of an immune response. The quantitative measurement of the amount of NF-κB in the nucleus versus the cytoplasm may, therefore, be extremely useful in the development of drugs that target immune function. Conventional high content screening systems are hindered in the analysis of NF-κB distribution due to the difficulty of imaging non-adherent immune cells on slides or plates and accurately measuring the quantity of NF-κB in the thin band of cytoplasm that characterize immune cells. The ImageStream platform, for example, eliminates these constraints with its ability to image non-adherent cells directly in suspension, its high resolution, and the statistical power (e.g., use of CCF) associated with its ability to analyze tens of thousands of cells.

Figure 11:
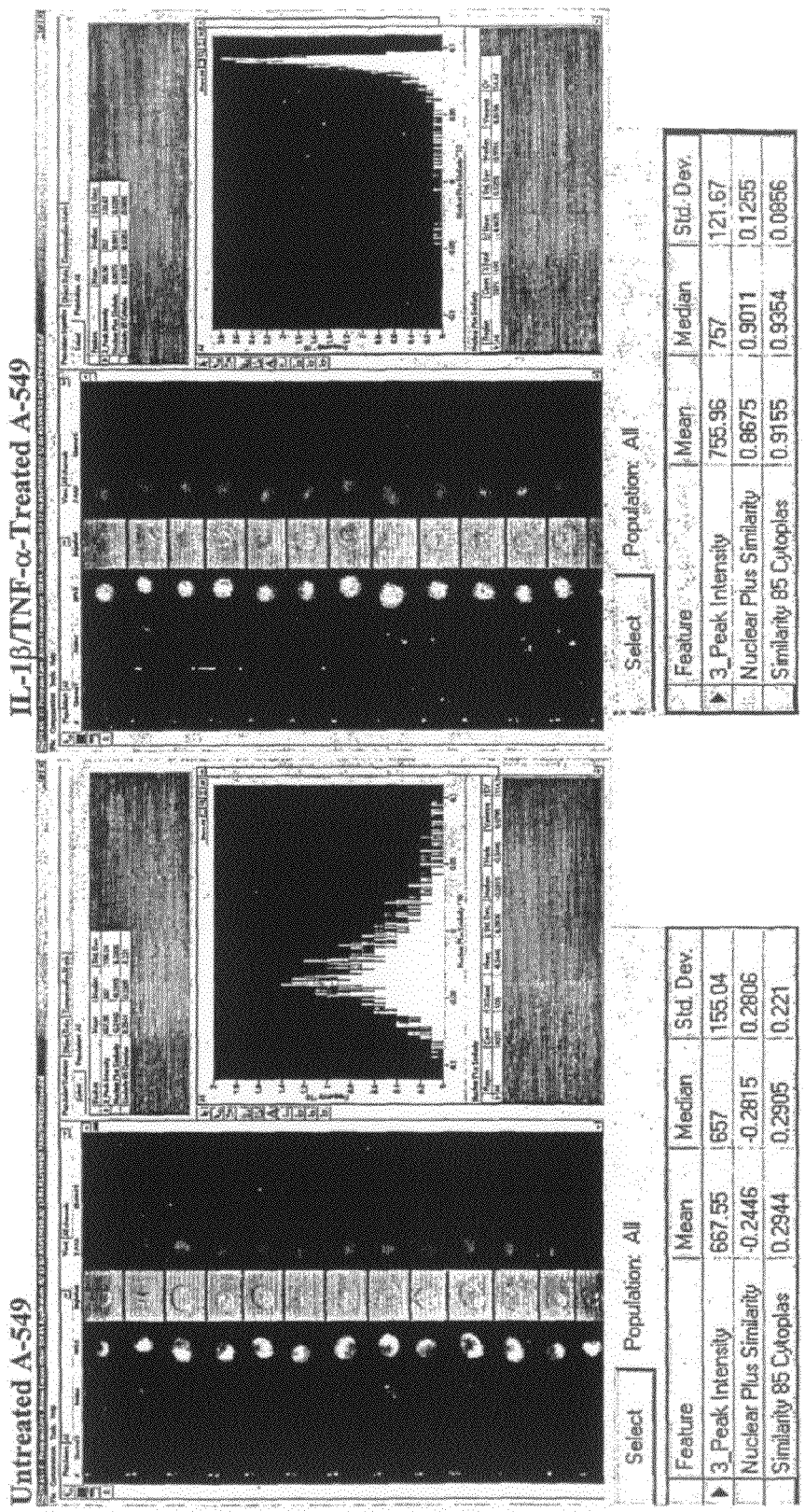
FIG. 11 shows images of nuclear translocation of NF-KB in adherent A-549 cells untreated (from left, first panel, images; second panel, quantitation of first panel images) and treated with IL-1β/TNF-α (third panel, images; fourth panel, quantitation of third panel images). Images are from darkfield, NF-κB labeled, brightfield, and 7-AAD nuclear labeled.

By way of background, it is well established that Tumor Necrosis Factor-α (TNF-α) and Interleukin 1-β (IL-1β) induce translocation of NPκB from the cytoplasm to the nucleus in many cell types. In FIG. 11, an adherent human lung carcinoma cell line A-549 was either not treated or treated for 1 hr with IL-1β and TNF-α. The cells were trypsinized and washed off the plate to adapt the cells to flow, and probed for NF-κB (stained with anti-NF-κB mAb—AF 488donkey anti-mouse IgG). The nucleus was also stained with 7-AAD. Using ImageStream and the CCF, a quantifiable difference in the nuclear localization NF-κB was observed when comparing untreated and IL-1β/TNF-α treated cells (see FIGS. 11 and 13). Thus, the methods of the present disclosure may be used with adherent cells and cell lines.

Figure 6:
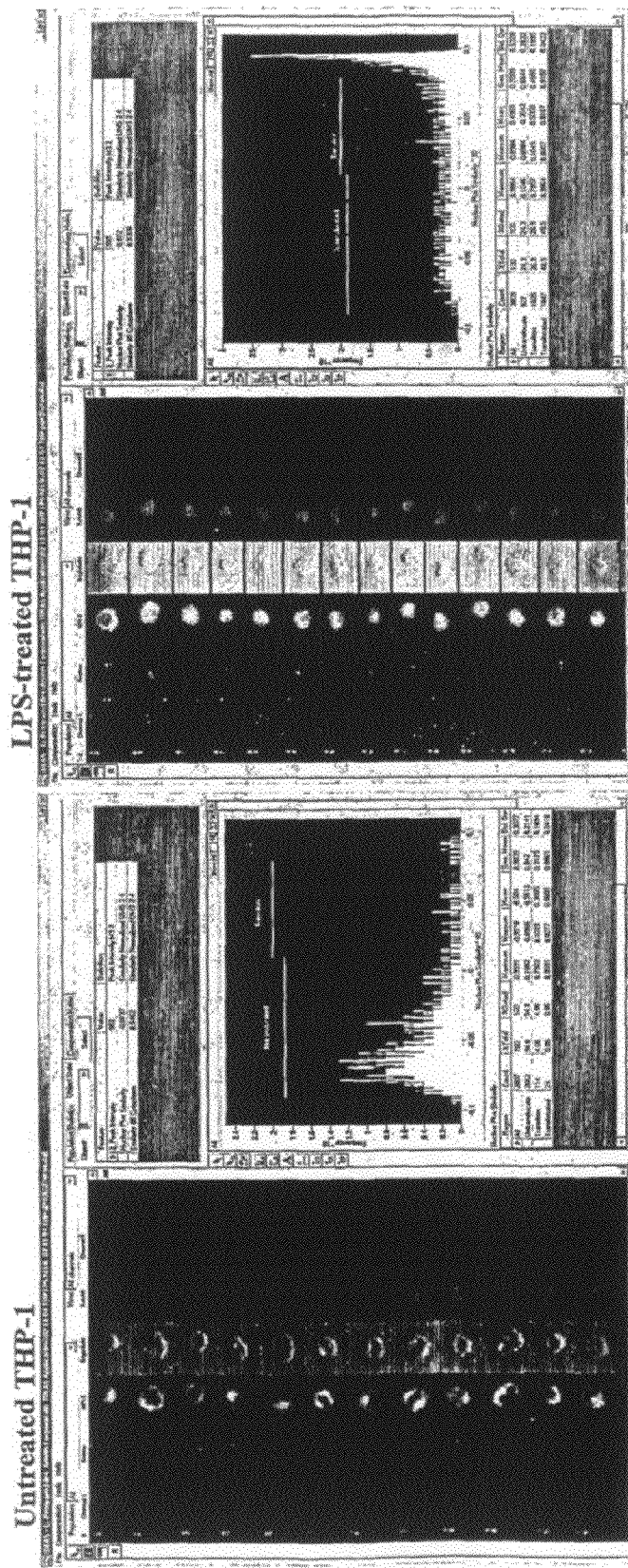
FIG. 6 shows nuclear translocation of NF-κB in THP-1 cells (monocyte cell line) untreated (from left, first panel, images; second panel, quantitation of first panel images) and treated with LPS (third panel, images; fourth panel, quantitation of third panel images). Images are from darkfield, NF-κB labeled, brightfield, and 7-AAD nuclear labeled.
Figure 10A:
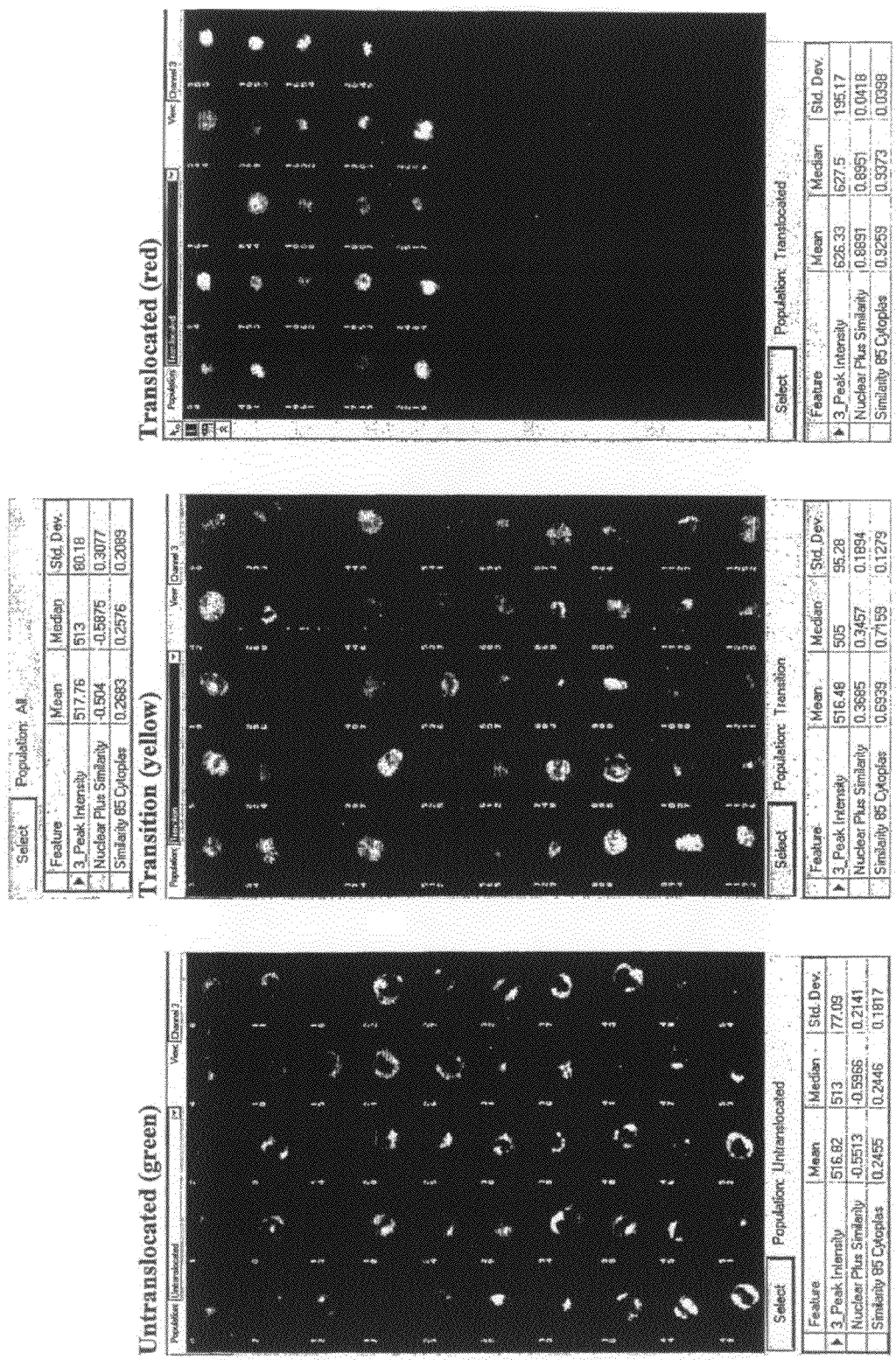
FIGS. 10A and 10B show imagery of THP-1 cells (A) untreated and (B) LPS-treated, and the three populations (untranslocated—green, transitional—yellow, and translocated—red) identified in the quantitation of FIG. 9.
Figure 10B:
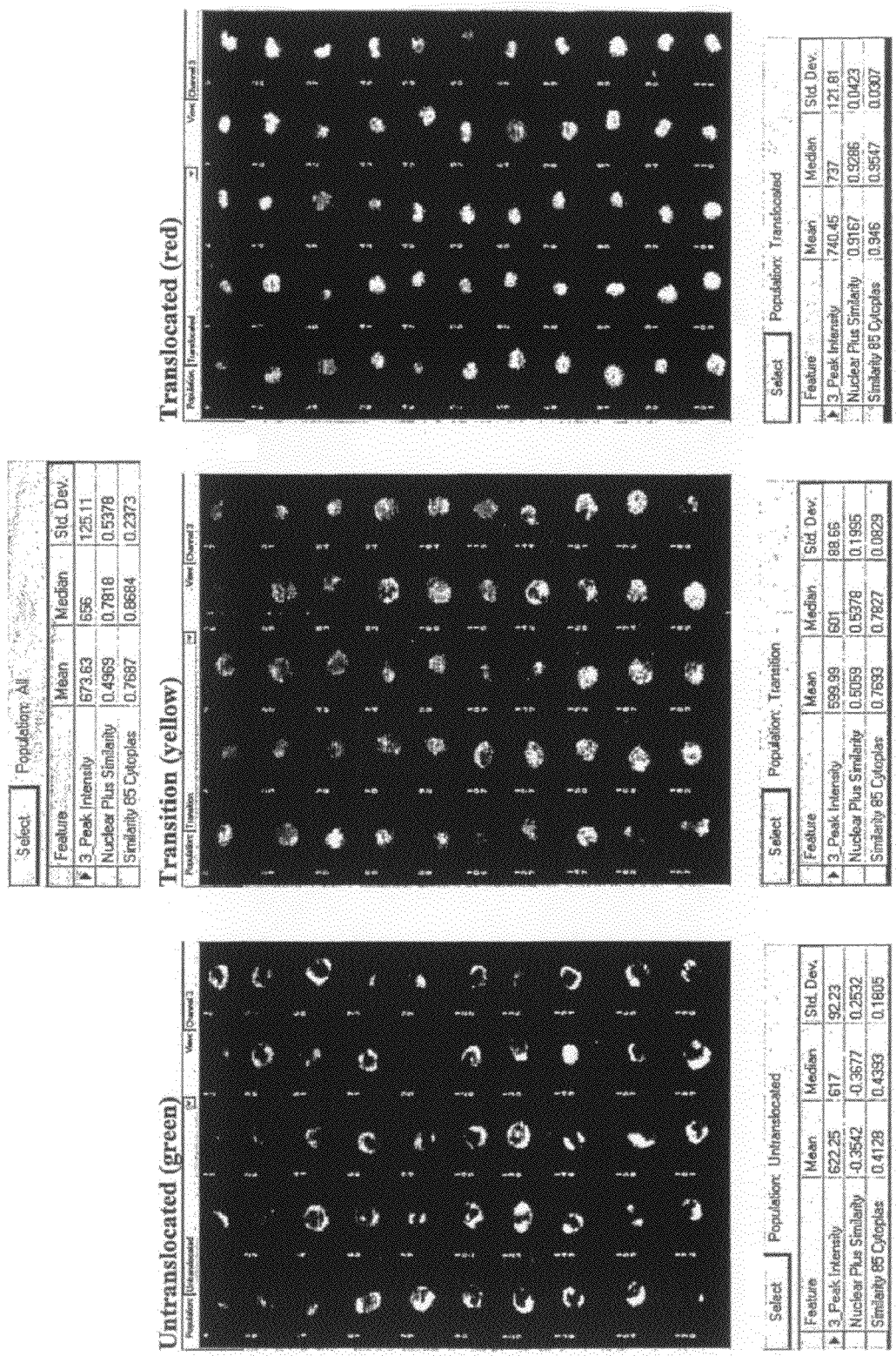

By way of background and wishing to be bound by theory, NF-κB resides predominantly in the cytoplasm in resting cells. Activating treatments (e.g., IL-1β/TNF-α or LPS) induce NF-κB translocation into the nucleus in responsive cell types. Thus, the ratio of nuclear to cytoplasmic NF-κB increases with LPS treatment. Similar to the A-549 cells, NF-κB is translocated from the cytoplasm to the nucleus when the non-adherent human monocyte cell line, THP-1, is exposed to lipopolysaccharide (LPS). Using the identical probing protocol and CCF, again a quantifiable difference in the nuclear localization NF-κB is demonstrated when comparing untreated and LPS-treated cells (see FIGS. 6 and 9). A nuclear and NF-κB pixel signal correlation analysis CCF was used to quantitate the difference between untranslocated NF-κB and NF-κB translocated to the cell nucleus. The CCF distinguished location-specific (nuclear and cytoplasmic) quantitation of NF-κB to distinguish LPS-treated from untreated THP-1 cells. Thus, the methods of the present disclosure may also be used with non-adherent cells and cell lines.

Classifier Approach: Compartmental Correlation Feature Scoring

The CCF is an algorithmic feature that correlates the variation of pixels (from the mean) across two channels, in this case the 7-AAD (nuclear) and NF-κB channels, within a generous 75% 7-AAD mask. This feature reduces cell-to-cell variation judgment calls associated with integrated nuclear to cytoplasmic NF-κB intensity ratios. This feature also avoids cell-to-cell variation in the inclusion/expulsion of background-like pixels associated with user defined NK-κB masks (see FIGS. 9 and 13).

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. The invention having been described, the following examples are intended to illustrate, and not limit, the invention.

EXAMPLES

Example 1

Induction of Translocation in Adherent Cells

Human lung carcinoma cell line A-549, obtained from ATCC (Rockville, Md.), was maintained in RPMI 1640 (Gibco, Grand Island, N.Y.) containing 5% fetal bovine serum, 1 mM sodium pyruvate (Mediatech, Herndon, Va.), 100 μM nonessential amino acids, 100 U/ml penicillin, 100 μg/ml streptomycin, and 2 mM L-glutamine (Bio Whittaker, Walkersville, Md.) in 5% $CO_2$ atmosphere at 37° C. The density of exponentially growing cells was less than $3\times10^5$ cells per ml at the time of all treatments. To induce NF-κB translocation into the nucleus from the cytoplasm, cells were treated for 1 hr with IL-1β and TNF-α.

The following is the experimental procedure for TNF-α/IL-1β induced Nuclear Translocation of NF-κB in A-549 cells Samples:
1) Unstained and single fluorescent color control samples—start with $3.0\times10^6$ total cells each. In this experiment, controls are: unstained
NFκB Alexa Fluor 488
7-AAD
At the end, resuspend in 100 μl 0.1% triton X-100/PBS.

Unstained and NFκB can be mixed and run as one file, then a separate .rif of unlabeled cells can be created in IDEAS. The 7-AAD control must be run separately, because 7-AAD comes off of labeled cells and stains unlabeled cells, confounding compensation. Furthermore, we run the sample with 7-AAD in the buffer to increase staining intensity (washing it away reduces the intensity about four-fold).
2) Experimental samples—start with $8\times10^6$ total cells for untreated and $10^7$ for TNF/IL-1 treated. Stain according to following protocol.
A-549 cells require special handling to resuspend properly. Resuspend pellets by pipeting up and down with a pipetman until cells appear dispersed. Then vortex.

A. Materials
  01. anti-NFκB (F6): Santa Cruz Biotechnology (Cat. No. SC-8008), 200 μg/ml
  02. Alexa Fluor 488 donkey anti-mouse IgG: Molecular Probes 1.1 mg/ml
  03. Streptavidin Alexa Fluor 488: Molecular Probes
  04. Recombinant human TNF-α: BD (Cat# 554618, Lot# 0000056653)
  05. Recombinant human IL-1☐: eBioscience (Cat# 14-8018-62)
  06. A549 cells (ATCC No. CCL-185)
  07. Dulbecco's MEM
  08. Fetal Calf Serum
  09. F-25 Culture Flask
  10. 0.25% trypsin/EDTA
  11. Phosphate buffered saline without $Ca^{2+}/Mg^{2+}$ (PBS)

12. 4% PFA/PBS (Fixation Buffer)
13. 0.1% triton X-100/PBS (Perm Buffer)

B. Cell Preparation

We used A549 cells cultured in Dulbecco's MEM supplemented with 10% fetal calf serum in an incubator containing 5% $CO_2$ at 37. A-549 cells were stimulated with or without TNF-α and IL-1β for 45 min to induce nuclear translocation of NF-κB.

01. Culture A549 cells in the T-75 $cm^2$ culture flask containing 20 ml of the 10% FCS/Dulbecco's MEM.
02. Stimulate the exponentially growing cells with TNF-α (2.0 ng/ml) and IL-1β (10 pg/ml) for 45 min at 37° C. under 5% $CO_2$ humidified atmosphere.
03. After stimulation, discard media and wash cells with 5-10 ml of PBS.
04. Add 2 ml of 0.25% trypsin/EDTA to cells, and incubate 37° C. for 1 min or until cells have detached.
05. Suspend cells by adding 8 ml of complete DMEM.
06. Transfer the cell suspension to 15 ml centrifuge tube.
07. Centrifuge at 300× g 10', 4° C., and remove media.
08. Fix cells by resuspending at $10^7$ cells/ml in 4% PFA/PBS 30', 4° C.
09. Wash with PBS, then perm cells by resuspending at 2×$10^7$ cells/ml in 0.1% triton X-100/0.02% EDTA/PBS (Perm) 30', 4° C.
10. Add equal volume of anti-NFκB 20 μg/mL in Perm (final mAb concentration of 10 μg/mL) 15', 4° C.
11. Wash Perm Buffer.
12. Resuspend $10^7$ cells/ml in Perm+AF 488 donkey anti-mouse IgG (10 μg/mL) 15', 4° C.
13. Filter 70 μm mesh and wash with Perm.
14. Resuspend 5×$10^7$ cells/ml Perm+10 μM 7-AAD 5' and run directly on the ImageStream.

Example 2

Induction of Translocation in Non-Adherent Cells

Human monocyte cell line THP-1, obtained from ATCC (Rockville, Md.), were maintained in RPMI 1640 (Gibco, Grand Island, N.Y.) containing 5% fetal bovine serum, 1 mM sodium pyruvate (Mediatech, Herndon, Va.), 100 μM nonessential amino acids, 100 U/ml penicillin, 100 μg/ml streptomycin, and 2 mM L-glutamine (BioWhittaker, Walkersville, Md.) in 5% $CO_2$ atmosphere at 37° C. The density of exponentially growing cells was less than 3×$10^5$ cells per ml at the time of all treatments. To induce NF-κB translocation into the nucleus from the cytoplasm, cells were treated for 1 hr with LPS.

The following is the experimental procedure for LPS-induced Nuclear Translocation of NF-κB in THP-1 cells.

Samples:

1) Unstained and single fluorescent color control samples—start with 3.0×$10^6$ total cells each. In this experiment, controls are:
unstained
NFκB Alexa Fluor488
7-AAD At the end, resuspend in 100 μl 0.1% triton X-100/PBS.

Unstained and NFκB can be mixed and run as one file, then a separate .rif of unlabeled cells can be created in IDEAS. The 7-AAD control must be run separately, because 7-AAD comes off of labeled cells and stains unlabeled cells, confounding compensation. Furthermore, we run the sample with 7-AAD in the buffer to increase staining intensity (washing it away reduces the intensity about four-fold).

2) Experimental samples—start with $10^7$ total cells for untreated LPS-treated. Stain according to following protocol.

A. Materials 1. anti-NFκB (F6): Santa Cruz Biotechnology (Cat. No. SC-8008), 200 μg/ml
2. Alexa Fluor 488 donkey anti-mouse IgG: Molecular Probes, 1.1 mg/ml
3. Streptavidin Alexa Fluor 488: Molecular Probes
4. Lipopolysaccharide (LPS) from *E. Coli* 0111 B4: Sigma (Cat# L2630)
5. THP-1 cells
6. RPMI
7. Fetal Calf Serum
8. T-75 $cm^2$ Culture Flask
9. EDTA
10. Phosphate buffered saline without $Ca^{2+}/Mg^{2+}$ (PBS)
11. 4% PFA/PBS (Fixation Buffer)
12. 0.1% triton X-100/PBS (Perm Buffer)

B. Cell Preparation

We used THP-1 cells cultured in RPMI supplemented with 10% fetal calf serum in an incubator containing 5% $CO_2$ at 37. THP-1 cells were stimulated with or without LPS and for 60 min to induce nuclear translocation of NF-κB.

1. Culture THP-1 cells in the T-75 $cm^2$ culture flask containing 50 ml of the 10% FCS/RPMI (3×$10^5$ cells/mL).
2. Stimulate the exponentially growing cells with LPS for 60 min at 37° C. under 5% $CO_2$ humidified atmosphere.
3. Centrifuge at 300× g 10', 4° C., and remove media.
4. Fix cells by resuspending at $10^7$ cells/ml in 4% PFA/PBS 30', 4° C.
5. Wash with PBS, then perm cells by resuspending at 2×$10^7$ cells/ml in 0.1% triton X-100/0.02% EDTA/PBS (Perm) 30', 4° C.
6. Add equal volume of anti-NFκB 20 μg/mL in Perm (final mAb concentration of 10 μg/mL) 15', 4° C.
7. Wash Perm Buffer.
8. Resuspend $10^7$ cells/ml in Perm+AF 488 donkey anti-mouse IgG (10 μg/mL) 15', 4° C.
9. Filter 70 μm mesh and wash with Perm.
10. Resuspend 5×$10^7$ cells/ml Perm+10 μM 7-AAD 5' and run directly on ImageStream.

Example 3

Nuclear Staining and NF-κB Staining

Control (untreated) cell and LPS or IL-1β/TNF-α treated cells were independently counted and washed once in phosphate buffered saline (PBS, Fair Lawn, N.J.). Each cell group was resuspended at $10^7$ cells/ml in 10 μM 7-aminoactinomycin D (7-AAD, Molecular Probes) for 10 minutes at room temperature. Cells were additionally stained with anti-NF-κB mAb—AF 488 donkey anti-mouse IgG. Each cell group was washed, fixed in 2% paraformaldehyde (Sigma), and analyzed by flow cytometry and immunofluorescence microscopy.

Example 4

Conventional Flow Cytometry and Imaging Flow Cytometry

For flow cytometry, cell fluorescence data excited by a 488 nm laser were acquired using the FACSort™ cytometer (BD Immunocytometry Systems, San Jose, Calif.) and analyzed using CellQuest™ (BD Immunocytometry Systems). For imaging flow cytometry, fixed cells at 5×$10^7$ cells per ml were run at 100 cells per second on an ImageStream100™ ("Beta"

version), and the data analyzed using the ImageStream Data Analysis and Exploration Software™ (IDEAS™).

Example 5

Instrumentation for Multispectral Imaging Flow Cytometry

Figures in U.S. Patent Application No. 2002/0146734 provide an exemplary layout of the ImageStream™ platform. Cells are hydrodynamically focused into a core stream and orthogonally illuminated for both darkfield and fluorescence imaging. The cells are simultaneously trans-illuminated via a spectrally-limited source (e.g., filtered white light or a light emitting diode) for brightfield imaging. Light is collected from the cells with an imaging objective lens and is projected on a charge-coupled detector (CCD). The optical system has a numeric aperture of 0.75 and the CCD pixel size in object space is 0.5 microns square, allowing high resolution imaging at event rates of approximately 100 cells per second. Each pixel is digitized with 10 bits of intensity resolution, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object.

Prior to projection on the CCD, the light is passed through a spectral decomposition optical system that directs different spectral bands to different lateral positions across the detector (see, e.g., U.S. Pat. No. 6,249,341). With this technique, an image is optically decomposed into a set of 6 sub-images, each corresponding to a different color component and spatially isolated from the remaining sub-images. This is exemplified in U.S. Patent Application No. 2002/0146734, which depicts a red brightfield illumination source and the associated transmitted light images in the red detector channel adjacent to fluorescent and scattered light images in the other spectral channels. The process of spectral decomposition occurs during the image formation process rather than via digital image processing of a conventional composite image.

The CCD is operated using time-delay-integration (TDI), in which image photons converted to photocharges in an array of pixels are continuously shifted (at a rate synchronized with the velocity of the flowing cell's image) from pixel to pixel down the detector and parallel to the axis of flow to avoid image streaking. For example, the instrument can operate at a continuous data rate of approximately 30 megapixels per second and integrate signal from each object for 10 milliseconds, which allows the detection of even faint fluorescent probes within cell images that are acquired at high speed. Attention to pump and fluidic system design to achieve highly laminar, non-pulsatile flow can eliminate cell rotation or lateral translation on the time scale of the imaging process (see, e.g., U.S. Pat. No. 6,532,061). Every pixel read from the CCD is analyzed by a real-time algorithm that detects the presence of object images and calculates a number of basic morphometric and photometric features, which can be used as criteria for data storage. Data files encompassing 10,000-20,000 cells can be about 100 MB in size, and are stored and analyzed using standard personal computers.

Example 6

Immunofluorescence Microscopy

Fixed control and treated cells were placed on a conventional glass slide (Erie Scientific, Portsmouth, N.H.), mixed 1:1 with Antifade (Molecular Probes) and covered with a cover slip. The cells were visualized at 400X using an Eclipse E600 (Nikon, Melville, N.Y.) fluorescence microscope equipped with filters appropriate for Alexa Fluor 488 (535/40 nm emission) and 7-AAD (630/60 nm emission).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for measuring molecular movement in a cell, comprising:
   contacting a cell with a compartment marker and with a molecular marker; imaging the marked cell with a detector;
   creating a compartment mask; and
   correlating said compartment mask and said molecular marker to measure molecular movement in a cell.

2. The method of claim 1 wherein there is relative motion between the cell and the detector.

3. The method of claim 1 wherein the molecular marker is a fluorescent labeled antibody.

4. The method of claim 1 wherein the compartment marker is a fluorescent molecule.

5. The method of claim 1 wherein the compartment marker is a nucleus, cytoplasm, or a membrane.

6. The method of claim 1 wherein the molecule marked is NF-κB.

7. The method of claim 1 further comprising the step of inducing molecular movement in the cell.

8. The method of claim 7 wherein the induced molecular movement is nuclear translocation.

9. The method of claim 7 wherein the molecular movement is induced with LPS or IL-1β/TNF-α.

10. A method for measuring nuclear translocation in a cell, comprising:
    contacting a cell with a nuclear marker and with a molecular marker;
    imaging the marked cell with a detector, creating a nuclear mask; and
    correlating said nuclear mask and said molecular marker to measure molecular movement in a cell.

11. The method of claim 10 wherein there is relative motion between the cell and the detector.

12. The method of claim 10 further comprising the step of inducing molecular movement in the cell.

13. The method of claim 12 wherein the induced molecular movement is nuclear translocation.

14. The method of claim 12 wherein the molecular movement is induced with LPS or IL-1β/TNF-α.

15. The method of claim 10 wherein the nuclear marker is 7-AAD.

16. The method of claim 10 wherein the molecule marked is NF-κB.

17. The method according to any one of claims 1-16 wherein the images are collected simultaneously.

18. The method according to any one of claims 1-16 wherein the detector is a time delay integration charge-coupled detector.

* * * * *